United States Patent
Wakamiya et al.

(10) Patent No.: US 8,231,830 B2
(45) Date of Patent: Jul. 31, 2012

(54) SAMPLE ANALYZER

(75) Inventors: Yuji Wakamiya, Kobe (JP); Tomohiro Okuzaki, Himeji (JP); Hisato Takehara, Kobe (JP)

(73) Assignee: Sysmex Corporation, Kobe (JP)

( * ) Notice: Subject to any disclaimer, the term of this patent is extended or adjusted under 35 U.S.C. 154(b) by 1140 days.

(21) Appl. No.: 12/050,791

(22) Filed: Mar. 18, 2008

(65) Prior Publication Data

US 2008/0240988 A1 Oct. 2, 2008

(30) Foreign Application Priority Data

Mar. 30, 2007 (JP) .................. 2007-092830

(51) Int. Cl.
*G01N 15/06* (2006.01)
*G01N 33/00* (2006.01)
*G01N 33/48* (2006.01)

(52) U.S. Cl. ............. 422/68.1; 422/50; 422/63; 422/64; 422/65; 422/66; 422/67; 422/81; 436/43; 436/47; 436/54; 436/63; 436/66; 436/67; 436/68; 436/69; 436/70; 436/71; 436/174; 436/180

(58) Field of Classification Search .............. 422/50, 422/63, 64, 65, 66, 67, 81, 82.01, 82.05, 422/68.1; 436/43, 47, 54, 63, 66, 67, 68, 436/69, 70, 71, 174, 180
See application file for complete search history.

(56) References Cited

U.S. PATENT DOCUMENTS

| 2003/0082662 | A1 | 5/2003 | Nakashima et al. | |
| 2004/0101440 | A1* | 5/2004 | Ishizawa et al. | 422/64 |
| 2005/0053521 | A1* | 3/2005 | Hirayama | 422/67 |
| 2005/0196821 | A1* | 9/2005 | Monfre et al. | 435/14 |
| 2006/0029520 | A1* | 2/2006 | Tanoshima et al. | 422/63 |
| 2006/0210438 | A1* | 9/2006 | Nagai et al. | 422/73 |
| 2007/0078631 | A1* | 4/2007 | Ariyoshi et al. | 702/189 |
| 2007/0110617 | A1* | 5/2007 | Nagai et al. | 422/65 |
| 2008/0056944 | A1* | 3/2008 | Nakamura et al. | 422/67 |
| 2008/0187951 | A1* | 8/2008 | Nagai et al. | 435/29 |
| 2008/0206098 | A1* | 8/2008 | Tsutsumida et al. | 422/67 |

FOREIGN PATENT DOCUMENTS

| JP | 01-227063 A | 9/1989 |
| JP | 10-282106 A | 10/1998 |
| JP | 2000-221198 A | 8/2000 |
| JP | 2003-315343 | 11/2003 |
| JP | 2004-317177 A | 11/2004 |

* cited by examiner

*Primary Examiner* — Brian J Sines
(74) *Attorney, Agent, or Firm* — Brinks Hofer Gilson & Lione

(57) ABSTRACT

A sample analyzer: measures a measurement sample including a sample and a reagent; creates a calibration curve based on first measurement data obtained by measuring a measurement standard sample including a standard sample and the reagent; provides calibration curve specifying information for specifying the calibration curve to the calibration curve; acquires an analysis result by processing second measurement data obtained by measuring the measurement sample based on the calibration curve; and stores the analysis result and the calibration curve specifying information provided to the calibration curve used in the process of the second measurement data in correspondence to each other.

12 Claims, 20 Drawing Sheets

| Sample | Specimen number | Concentration | Order | Number of measurements |
|---|---|---|---|---|
| C0 | STD-0 | 0.000 | ⌄ | 5 ▲ |
| C1 | STD-1 | 0.250 | ⌄ | 5 ▲ |
| C2 | STD-2 | 2.500 | ⌄ | 1 ▲ |
| C3 | STD-3 | 25.000 | ⌄ | 1 ▲ |
| C4 | STD-4 | 250.000 | ⌄ | 1 ▲ |
| C5 | STD-5 | 2500.000 | ⌄ | 1 ▲ |

Calibration curve measurement order setting

Calibration curve order input

Input rack number: 123456 key

Specimen position: ◀ 10 ▶

Item specification
Item name: HBsAg ▲

Reagent lot

| Reagent type | Lot number |
|---|---|
| R1, R2, R3 | HBsAg ▲ |
| R4, R5 | HBsAg |
| Calibrator | HBsAg ▲ |

Creating method: Full calibration ▲

OK   Cancel

Calibration curve validation

Calibration curve of display target will now be validated.
Select storing destination of the validated calibration curve.

Calibration curve storing destination

Select storing destination: ● Lot #1   ○ Lot #2

| | Lot #1 | Lot #2 |
|---|---|---|
| Calibration curve ID | 12345 | 99999 |
| State | Validated | not Validated |
| Created date and time | 2007/12/31 23:58 | 2008/01/01 00:01 |
| Validated date and time | 2007/12/31 23:59 | |
| Expiration date | 2008/01/31 | |
| Creating method | 2P Correct | Manual |
| R1, R2, R3 | QQ1111 | WW4444 |
| R4, R5 | AA2222 | XX6666 |
| Calibrator | EE6666 | DD7777 |

[ OK ]   [ Cancel ]

| Item name | Analyzed time | Analysis result | Unit | Determination | Dilution | Calibration curve ID | Count value | R1,R2,R3 | R4,R5 | Error |
|---|---|---|---|---|---|---|---|---|---|---|
| HBsAg | 00:20:21 | 190.417 | IU/mL | + | 1/1 | 12345 | 1,234,567.890 | 001111 | WW9999 | |
| HBsAb | 00:20:39 | 13.20 | mIU/mL | − | 1/1000 | 99999 | 10.000 | ZZZZZZ | XX3456 | |
| HBeAg | | | | | | | | | | |
| HBeAb | | | | | | | | | | |
| HBcAb | | | | | | | | | | |
| HCV | | | | | | | | | | |

10: Comment on measurement result

Calibration curve recycle

Calibration curve selection

Item name: HBsAg

☑ Selecting condition specification

● Specification of calibration curve ID

Calibration curve ID: 12345

○ Specification other than calibration curve ID

☑ Validated date
Start 2007/01/01
End 2007/12/31

☑ R1, R2, R3  QQ1111
☑ R4, R5  QQ1111
☐ Calibrator  RR4444

| ID | Validated date and time | R1, R2, R3 | R4, R5 | Calibrator | Instrument |
|----|-------------------------|------------|--------|------------|------------|
| 12345 | 2008/12/20 12:59 | QQ1111 | WW9999 | RR4444 | No. 1 |
|  |  |  |  |  |  |
|  |  |  |  |  |  |
|  |  |  |  |  |  |
|  |  |  |  |  |  |
|  |  |  |  |  |  |
|  |  |  |  |  |  |
|  |  |  |  |  |  |
|  |  |  |  |  |  |

[ OK ]   [ Cancel ]

FIG.20

SAMPLE ANALYZER

RELATED APPLICATIONS

This application claims priority under 35 U.S.C. §119 to Japanese Patent Application No. 2007-092830 filed Mar. 30, 2007, the entire content of which is hereby incorporated by reference.

FIELD OF THE INVENTION

The present invention relates to a sample analyzer for analyzing samples such as immune analyzer and blood coagulation analyzer.

BACKGROUND

In great number of sample analyzers including immune analyzer and blood coagulation analyzer, the measurement data of the sample measured by a measurement unit of the analyzer is converted using calibration curve obtained in advance to obtain the desired analysis result. For instance, in the immune analyzer which performs examinations on items such as hepatitis B and tumor marker using blood, the light emission amount data (number of photons) of the sample obtained through measurement of light emission amount is converted to the concentration of a predetermined substance using the calibration curve obtained by measuring a standard sample (calibrator) which concentration is already known.

Normally, the most recent calibration curve is used for analysis, where if the most recent calibration curve is inappropriate (when lots of the reagent of when the calibration curve is created and the reagent used in measurement differ, when the time the calibration curve is created is old, etc.), the analysis result obtained using such calibration curve also becomes inappropriate, and such analysis result cannot be used. Japanese Laid-Open Patent Publication No. 2003-315343 discloses an automatic analyzer which judges the validity of the calibration curve with reagent lot or expiration date of the calibration curve as criterion of judgment, and performs a control to not use the relevant calibration curve if the conditions of validity are not met.

If an appropriate calibration curve does not exist, a new calibration curve is created after analyzing the sample by ex-post measuring the calibrator, and re-analysis (conversion) of the measurement data is performed based on the new calibration curve.

However, in the analyzer using the calibration curve of the prior art including the analyzer disclosed in Japanese Laid-Open Patent Publication No. 2003-315343, although the desired output of "analysis result" can be obtained, the used calibration curve cannot be specified when attempting to trace the analysis result since the configuration is not such which stores the calibration curve used for the analysis. Therefore, even if abnormality is found in the analysis result, the investigation for the cause of abnormality was limited.

SUMMARY OF THE INVENTION

The scope of the present invention is defined solely by the appended claims, and is not affected to any degree by the statements within this summary.

A first aspect of the present invention is a sample analyzer comprising: a measurement unit for measuring a measurement sample including a sample and a reagent; a calibration curve creating means for creating a calibration curve based on first measurement data obtained by measuring a measurement standard sample including a standard sample and the reagent by the measurement unit; a calibration curve specifying information providing means for providing calibration curve specifying information for specifying the calibration curve to the calibration curve created by the calibration curve creating means; a measurement data processing means for acquiring an analysis result by processing second measurement data obtained by measuring the measurement sample by the measurement unit based on the calibration curve created by the calibration curve creating means; and an analysis result storage means for storing the analysis result acquired by the measurement data processing means and the calibration curve specifying information provided to the calibration curve used in the process of the second measurement data in correspondence to each other.

A second aspect of the present invention is a sample analyzer comprising: a measurement unit for measuring a measurement sample including a sample and a reagent; a calibration curve creating means for creating a calibration curve based on first measurement data obtained by measuring a measurement standard sample including a standard sample and the reagent by the measurement unit; a first storage means for storing the calibration curve which can be used for analysis; a second storage means for storing a plurality of second calibration curves used in the past; a designation accepting means for accepting designation of a specific calibration curve from the plurality of second calibration curves stored in the second storage means; a calibration curve recycling means for storing the specific calibration curve specified from the plurality of second calibration curves stored in the second storage means to the first storage means as the calibration curve which can be used for analysis; and a measurement data processing means for acquiring an analysis result by processing the second measurement data obtained by measuring the measurement sample by the measurement unit based on the calibration curve recycled by the calibration curve recycling means.

A third aspect of the present invention is a sample analyzer comprising: a measurement unit for measuring a measurement sample including a sample and a reagent; a calibration curve creating means for creating a calibration curve based on first measurement data obtained by measuring a measurement standard sample including a standard sample and the reagent by the measurement unit; a first storage means for storing the calibration curve which can be used for analysis; a second storage means for storing the first measurement data of the plurality of standard samples used in creating a plurality of second calibration curves used in the past; a designation accepting means for accepting designation of a specific first measurement data from the plurality of first measurement data stored in the second storage means; and a calibration curve recycling means for creating a third calibration curve based on the specific first measurement data specified from the plurality of first measurement data stored in the second storage means, and storing the third calibration curve in the first storage means as the calibration curve which can be used for analysis; and a measurement data processing means for acquiring an analysis result by processing the second measurement data obtained by measuring the measurement sample with the measurement unit based on the calibration curve reproduced by the calibration curve recycling means.

BRIEF DESCRIPTION OF THE DRAWINGS

FIG. 11 is a view showing an example of an order registration screen;

FIG. 12 is a view showing an example of a calibration curve order input dialogue;

FIG. 15 is a view showing an example of a validation dialogue of the calibration curve;

FIG. 19 is a view showing a browser screen; and

FIG. 20 is a view showing an example of a recycle dialogue.

DETAILED DESCRIPTION OF THE PREFERRED EMBODIMENTS

The preferred embodiments of the present invention will be described hereinafter with reference to the drawings.

[Overall Configuration of Apparatus]

Figure 1:
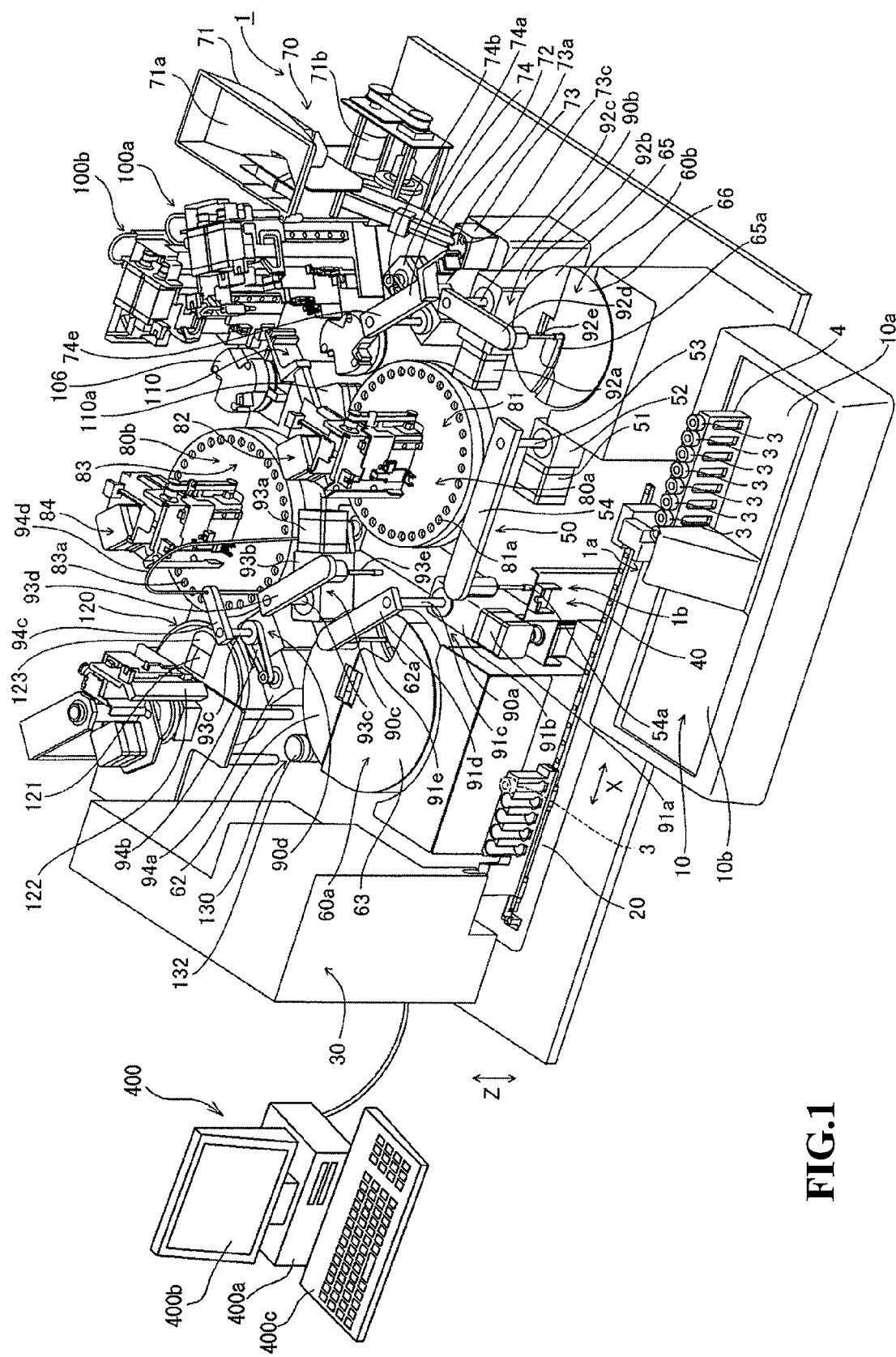
FIG. 1 is a perspective view showing an overall configuration of one embodiment of a sample analyzer of the present invention.
Figure 2:
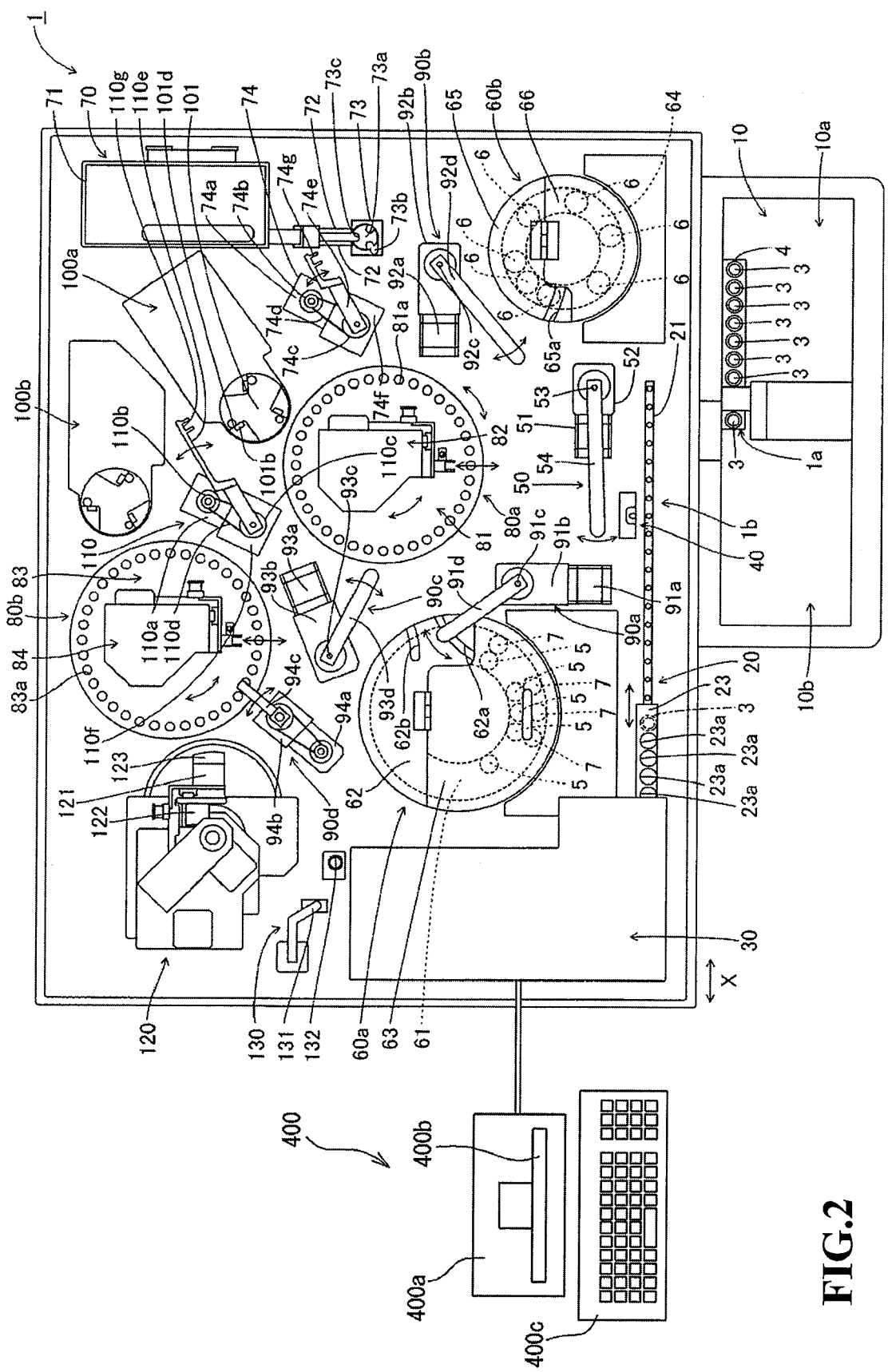
FIG. 2 is a plan view showing an overall configuration of an immune analyzer shown in FIG. 1.
Figure 3:
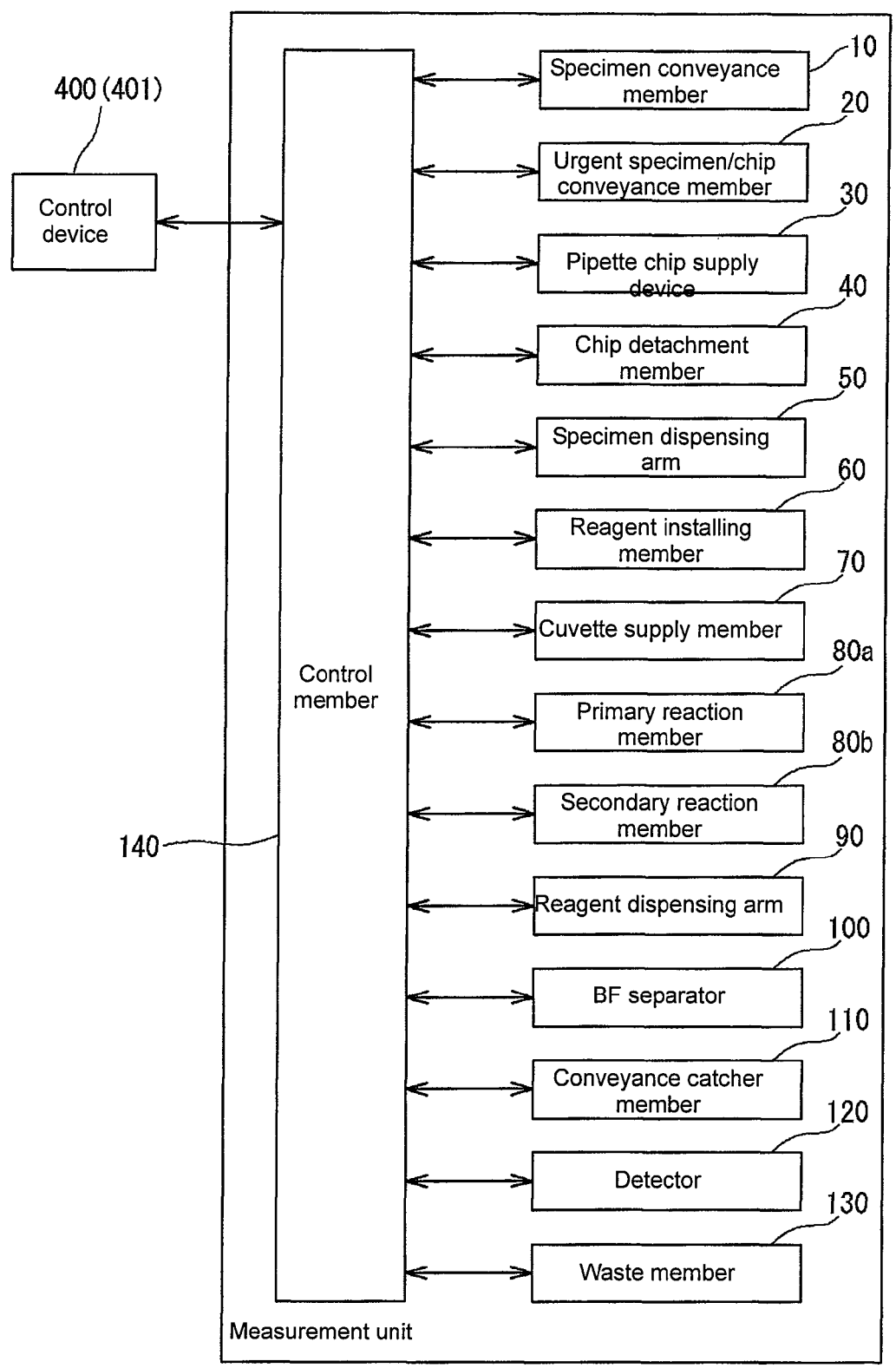
FIG. 3 is a block diagram showing a configuration of a measurement unit in the immune analyzer shown in FIG. 1.

An immune analyzer 1 according to one embodiment of the present invention is an apparatus for carrying out examinations on various items such as hepatitis B, hepatitis C, tumor marker, and thyroid hormone using specimen such as blood. As shown in FIGS. 1 and 2, the immune analyzer 1 is mainly configured by a measurement unit including a specimen conveyance member (sampler) 10, an urgent specimen/chip conveyance member 20, a pipette chip supply device 30, a chip detachment member 40, a specimen dispensing arm 50, reagent installing members 60a and 60b, a cuvette supply member 70, a primary reaction member 80a and a secondary reaction member 80b, reagent dispensing arms 90a, 90b, 90c, and 90d, BF separators 100a and 100b, a conveyance catcher member 110, a detector 120, a waste member 130, a control section 140 (see FIG. 3) for performing operation control of mechanisms such as the specimen conveyance member (sampler) 10 and the specimen dispensing arm 50; and a control device 400 (see FIG. 4) electrically connected to the measurement unit. In the immune analyzer 1 according to the present embodiment, the disposable pipette chip 2 (see FIG. 5) is changed every time suction and discharge of specimen are performed in order to suppress the specimen such as blood suctioned and discharged by the specimen dispensing arm 50 from mixing with other specimen.

In the immune analyzer 1, magnetic particles (R2 reagent) are bonded to a trapped antibody (R1 reagent) bonded to an antigen contained in a specimen such as blood, which is the measuring object, and thereafter, the bound antigen, the trapped antibody, and the magnetic particles are attracted to a magnet 101b of a BF (Bound Free) separator 100a to remove the R1 reagent containing non-reactive (free) trapped body. A labeled antibody (R3 reagent) is bonded to the antigen bound with magnetic particles, and thereafter, the bound magnetic particles, the antigen, and the labeled antibody are attracted to a magnet of a BF separator 100b to remove the R3 reagent containing non-reactive (free) labeled antibody. Furthermore, a luminescent substrate (R5 reagent) that emits light in the reaction process with the labeled antibody is added, and a light emission amount generated through the reaction of the labeled antibody and the luminescent substrate is measured. Through such processes, the antigen contained in the specimen that bonds with the labeled antibody is quantitatively measured.

[Configuration of Control Device]

The control device 400 is configured by a personal computer 401 (PC), and includes a control section 400a, a display member 400b, and a keyboard 400c, as shown in FIG. 1. The control section 400a has a function of performing operation control of each mechanism in the measurement unit, and analyzing optical information of the specimen obtained in the measurement unit. The control section 400a consists of CPU, ROM, RAM, and the like. The display member 400b is provided to display the analysis result obtained by the control section 400a, and to display graphs etc. of the calibration curve to be hereinafter described.

Figure 4:
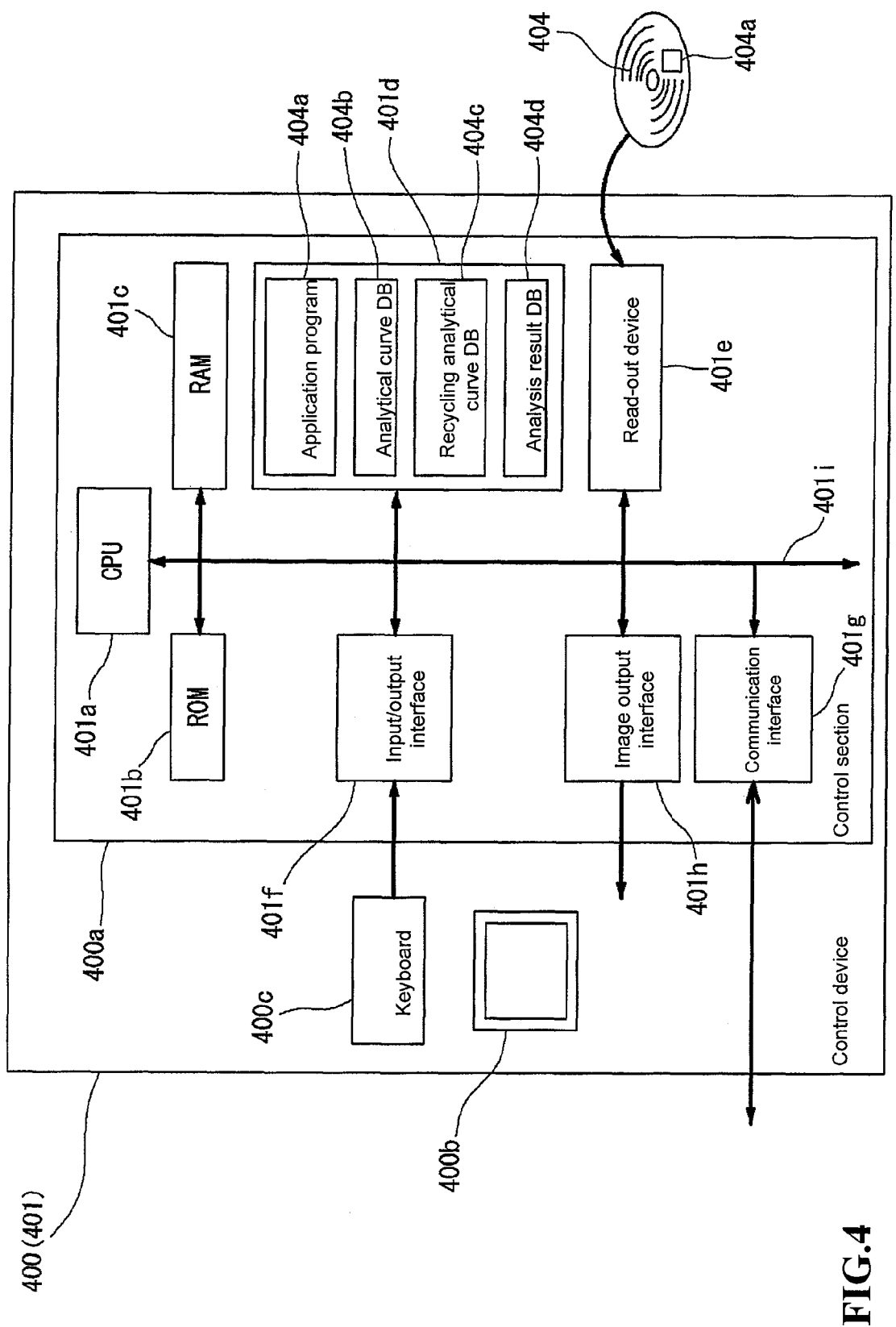
FIG. 4 is a block diagram of a control device in the immune analyzer shown in FIG. 1.
Figure 5:
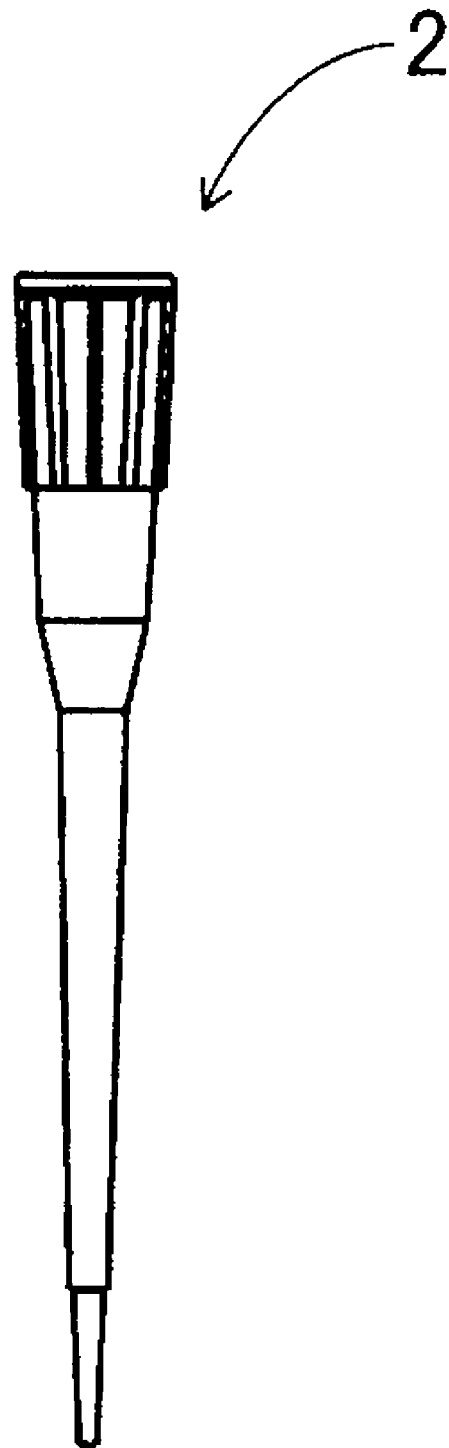
FIG. 5 is a front view of a pipette chip supplied by a pipette chip supply device of the immune analyzer shown in FIG. 1.

The configuration of the control device 400 will now be described. As shown in FIG. 4, the control section 400a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a executes computer programs stored in the ROM 401b and the computer programs loaded in the RAM 401c. The computer 401 serves as the control device 400 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The application program 404a for providing specifying information to the calibration curve and recycling the calibration curve according to the present embodiment is also installed in the hard disc 401d.

The read-out device 401e is configured by flexible disc drive, CD-ROM drive, DVD-ROM drive, and the like, and is able to read out computer programs and data recorded on a portable recording medium 404. The application program 404a according to the present embodiment is stored in the portable recording medium 404, where the computer 401 reads out the application program 404a from the portable recording medium 404, and installs the application program 404a to the hard disc 401d.

The application program 404a is not only provided by the portable recording medium 404, but is also provided through communication line (wired or wireless) from external devices communicatably connected with the computer 401 through the communication line. For instance, the application program 404a may be stored in the hard disc of the server computer on the Internet, so that the computer 401 can access the server computer to download the application program 404a and install the application program 404a to the hard disc 401d.

Operating system providing graphical user interface environment such as Windows manufactured and sold by US Microsoft Co. is installed in the hard disc 401d. In the following description, the application program 404a according to the present embodiment is assumed to operate on the operating system.

Calibration curve database 404b for storing calibration curves that can be currently used, recycling calibration curve database 404c for storing calibration curves that have been used in the past, and analysis result database 404d for storing analysis result are stored in the hard disc 401d. The configurations of the calibration curve database 404b, the recycling calibration curve database 404c, and the analysis result database 404d will be hereinafter described.

The input/output interface 401f is configured by serial interface such as USB, IEEE1394, RS-232C; parallel interface such as SCSI, IDE, IEEE1284; analog interface such as D/A converter, A/D converter, and the like. The keyboard 400c is connected to the input/output interface 401f, so that the user can input data to the computer 401 using the keyboard 400c.

The communication interface 401g is, for example, Ethernet (registered trademark) interface. The computer 401 transmits and receives data with the measurement unit using a predetermined communication protocol by means of the communication interface 401g.

The image output interface 401h is connected to the display member 400b configured by LCD, CRT, or the like, and is configured to output an image signal corresponding to the image data provided from the CPU 401a to the display member 400b. The display member 400b displays the image (screen) according to the input image signal.

[Configuration of Each Mechanism of the Immune Analyzer]

As shown in FIGS. 1 and 2, the specimen conveyance member 10 is configured to convey a rack 4 mounted with a plurality of test tubes 3 accommodating the specimen to a position corresponding to a suction position 1a of the specimen dispensing arm 50. The specimen conveyance member 10 includes a rack set section 10a for setting the rack 4 mounted with the test tube 3 accommodating un-processed specimen, and a rack storage section 10b for storing the rack 4 mounted with the test tube 3 accommodating dispense processed specimen.

When the test tube 3 accommodating the non-processed specimen is conveyed to the position corresponding to the suction position 1a of the specimen dispensing arm 50, the specimen such as blood in the test tube 3 is suctioned by the specimen dispensing arm 50, and the rack 4 mounted with the relevant test tube 3 is stored in the rack storage section 10b.

The urgent specimen/chip conveyance member 20 is configured to convey the test tube 3 accommodating urgent specimen that needs to be cut into the specimen being conveyed by the specimen conveyance member 10 for examination to an attachment position 1b of the specimen dispensing arm 50.

The pipette chip supply device 30 has a function of mounting the placed pipette chip 2 (see FIG. 5) on a chip installing section 23b of a conveyance rack 23 of the urgent specimen/chip conveyance member 20 one at a time through a shoot 31.

The chip detachment member 40 (see FIGS. 1 and 2) is provided to detach the pipette chip 2 (see FIG. 5) attached to the specimen dispensing arm 50 to be hereinafter described.

Figure 6:
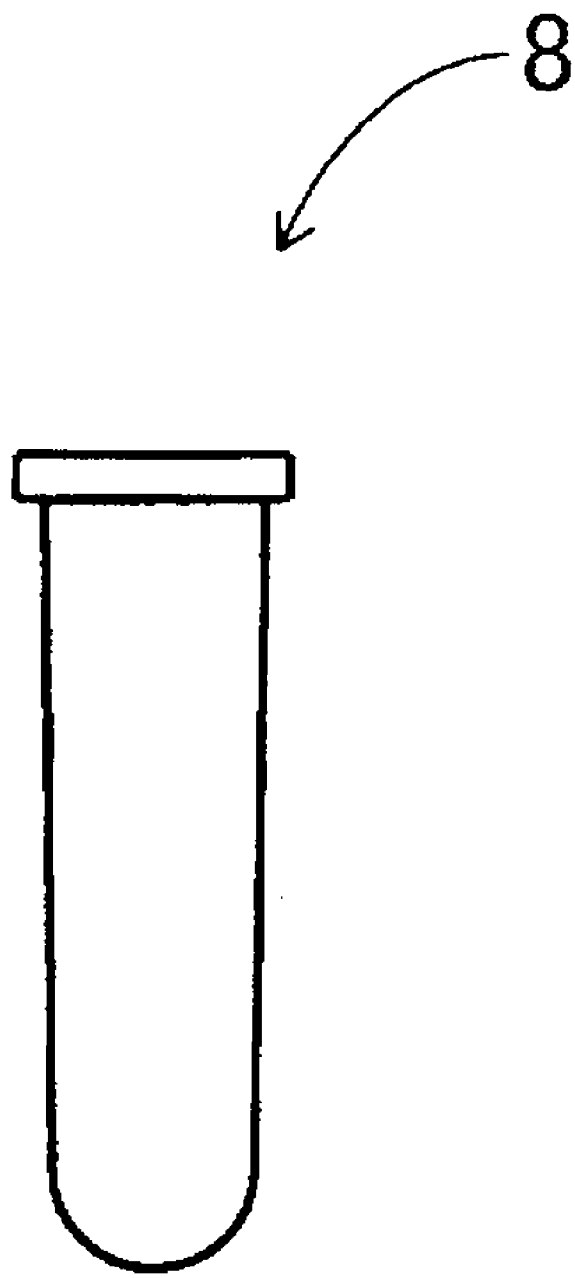
FIG. 6 is a front view of a cuvette supplied by a cuvette supply device of the immune analyzer shown in FIG. 1.

The specimen dispensing arm 50 (see FIGS. 1 and 2) has a function of dispensing the specimen in the test tube 3 conveyed to the suction position 1a by the specimen conveyance member 10 into a cuvette 8 (see FIG. 6) held by a holder 81a of a rotatable table 81 of the primary reaction member 80a to be hereinafter described. As shown in FIGS. 1 and 2, the specimen dispensing arm 50 includes a motor 51, a drive transmitting part 52 connected to the motor 51, and an arm 54 attached to the drive transmitting part 52 by way of a shaft 53. The drive transmitting part 52 is configured to turn the arm 54 with the shaft 53 as the center by the driving force from the motor 51, and move the arm in the up and down direction (Z direction). A nozzle 54a for suctioning and discharging the specimen is arranged at the distal end of the arm 54. The pipette chip 2 (see FIG. 5) conveyed by a conveyance rack (not shown) of the urgent specimen/chip conveyance member 20 is attached to the distal end of the nozzle 54a.

The reagent installing member 60a (see FIGS. 1 and 2) includes an installing section 61 for installing a reagent container 5 (see FIG. 2) accommodating the R1 reagent including trapped antibody and a reagent container 7 (see FIG. 2) accommodating the R3 reagent containing labeled antibody; an upper surface 62 arranged on the upper part of the installing section 61 so that foreign substances such as dust does not enter the R1 reagent in the reagent container 5 or the R3 reagent in the reagent container 7 installed in the installing section 61; and a lid 63 attached in an openable/closable manner to the upper surface 62. A groove 62a to be inserted with a nozzle 91e of the reagent dispensing arm 90a, to be hereinafter described, and a groove 62b (see FIG. 2) to be inserted with a nozzle 93e of the reagent dispensing arm 90c are formed in the upper surface 62. The installing section 61 is rotatably configured to convey the installed reagent container 5 and the reagent container 7 to positions corresponding to the groove 62a and the groove 62b of the upper surface 62, respectively.

The reagent installing member 60b (see FIGS. 1 and 2) includes an installing section 64 for installing a reagent container 6 (see FIG. 2) accommodating the R2 reagent containing magnetic particles; an upper surface 65 arranged on the upper part of the installing section 64 so that foreign substances such as dust does not enter the R2 reagent in the reagent container 6 installed in the installing section 64; and a lid 66 attached in an openable/closable manner to the upper surface 65. A groove 65a to be inserted with a nozzle 92e of the reagent dispensing arm 90b, to be hereinafter described is formed in the upper surface 65. The installing section 64 is rotatably configured to convey the installed reagent container 6 to a position corresponding to the groove 65a of the upper surface 65.

The cuvette supply member 70 (see FIGS. 1 and 2) is configured so as to sequentially supply a plurality of cuvettes 8 (see FIG. 6) to the holder 81a of the rotatable table 81 of the primary reaction member 80a. The cuvette supply member 70 includes a hopper feeder 71 capable of accommodating the plurality of cuvettes 8, two inductive plates 72 arranged on the lower side of the hopper feeder 71, a supporting board 73 arranged on the lower end of the inductive plate 72, and a supply catcher section 74.

As shown in FIGS. 1 and 2, the supply catcher section 74 has a function of transporting the cuvette 8 (see FIG. 6) received by a concave part 73b to the holder 81a of the rotatable table 81 of the primary reaction member 80a. The supply catcher section 74 includes a motor 74a, a pulley 74b connected to the motor 74a, a pulley 74c arranged with a predetermined spacing from the pulley 74b, a drive transmission belt 74d attached to the pulley 74b and the pulley 74c, an arm 74e attached to the pulley 74c by way of a shaft, and a drive part 74f for moving the arm 74e in the up and down direction. A chuck part 74g for sandwiching and gripping the cuvette 8 is arranged at the distal end of the arm 74e.

The primary reaction member 80a is arranged to rotatably transport the cuvette 8 held at the holder 81a of the rotatable table 81 by a predetermined angle for every predetermined period (18 seconds in the present embodiment), and to stir the specimen, the R1 reagent, and the R2 reagent in the cuvette 8. That is, the primary reaction member 80a is arranged to react the R2 reagent including magnetic particles and the antigen in the specimen in the cuvette 8. The primary reaction member 80a is configured by the rotatable table 81 for conveying the cuvette 8 accommodating the specimen, the R1 reagent, and the R2 reagent in the rotating direction, and a container conveyance section 82 for stirring the specimen, the R1 reagent, and the R2 reagent in the cuvette 8 and conveying the cuvette 8 accommodating the stirred specimen, the R1 reagent, and the R2 reagent to the BF separator 100a (see FIGS. 1 and 2) to be hereinafter described.

The container conveyance section 82 is rotatably installed at the center of the rotatable table 81. The container conveyance section 82 has a function of gripping the cuvette 8 held at the holder 81a of the rotatable table 81 and stirring the sample in the cuvette 8. The container conveyance section 82 also has a function of conveying the cuvette 8 accommodating the sample obtained by stirring and incubating the specimen, the R1 reagent, and the R2 reagent to the BF separator 100a (see FIGS. 1 and 2).

The reagent dispensing arm 90a (see FIGS. 1 and 2) has a function of suctioning the R1 reagent in the reagent container 5 installed in the installing section 61 of the reagent installing member 60a, and dispensing the suctioned R1 reagent into the cuvette 8 dispensed with the specimen of the primary reaction member 80a. The reagent dispensing arm 90a includes a motor 91a, a drive transmitting part 91b connected to the motor 91a, and an arm 91d attached to the drive transmitting part 91b by way of a shaft 91c. The drive transmitting part 91b is configured to turn the arm 91d with the shaft 91c as the center by the driving force from the motor 91a, and move the arm in the up and down direction. A nozzle 91e for suctioning and discharging the R1 reagent in the reagent container 5 is attached to the distal end of the arm 91d. That is, the nozzle 91e is configured to suction the R1 reagent in the reagent container 5 through the groove 62a of the upper surface 62 of the reagent installing member 60a, and thereafter, dispense the suctioned R1 reagent into the cuvette 8 dispensed with the specimen.

The reagent dispensing arm 90b (see FIGS. 1 and 2) has a function of dispensing the R2 reagent in the reagent container 6 installed in the installing section 64 of the reagent installing member 60b into the cuvette 8 dispensed with the specimen and the R1 reagent of the primary reaction member 80a. The reagent dispensing arm 90b includes a motor 92a, a drive transmitting part 92b connected to the motor 92a, and an arm 92d attached to the drive transmitting part 92b by way of a shaft 92c. The drive transmitting part 92b is configured to turn the arm 92d with the shaft 92c as the center by the driving force from the motor 92a, and move the arm in the up and down direction. A nozzle 92e for suctioning and discharging the R2 reagent in the reagent container 6 is attached to the distal end of the arm 92d. Therefore, the nozzle 92e is configured to suction the R2 reagent in the reagent container 6 through the groove 65a of the upper surface 65 of the reagent installing member 60b, and thereafter, dispense the suctioned R2 reagent into the cuvette 8 dispensed with the specimen.

Figure 7:
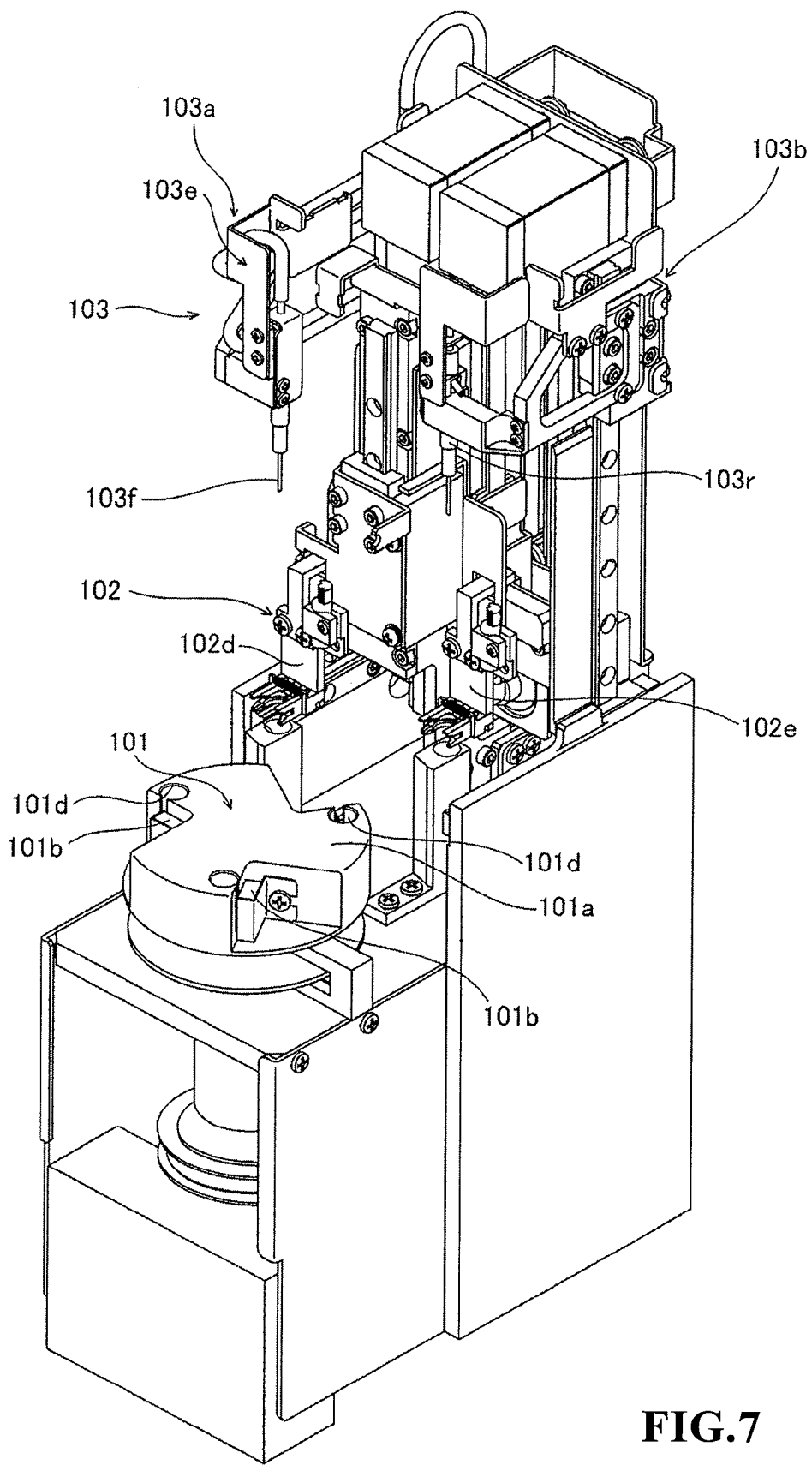
FIG. 7 is a perspective view showing a BF separator of the immune analyzer shown in FIG. 1.

In the present embodiment, the BF separator 100a (see FIGS. 1 and 2) is arranged to separate the non-reactive R1 reagent (unnecessary component) and the magnetic particles from the sample in the cuvette 8 (see FIG. 6) conveyed by the container conveyance section 82 of the primary reaction member 80a. As shown in FIG. 7, the BF separator 100a includes a magnet collecting section 101 for installing and conveying the cuvette 8 in the rotating direction, a stirring mechanism section 102 for stirring the sample in the cuvette 8, a separation mechanism section 103 for suctioning the sample in the cuvette 8 and discharging washing liquid, and nozzle washing sections 104a and 104b.

The conveyance catcher member 110 (see FIGS. 1 and 2) has a function of conveying the cuvette 8 (see FIG. 6) of the magnet collecting section 101 of the BF separator 100a in which non-reactive R1 reagent etc. is separated to a holder 83a of a rotatable table 83 of the secondary reaction member 80b. The conveyance catcher member 110 includes a motor 110a, a pulley 110b connected to the motor 110a, a pulley 110c arranged with a predetermined spacing from the pulley 110b, a drive transmission belt 110d attached to the pulley 110b and the pulley 110c, an arm 110e attached to the pulley 110c by way of a shaft, and a drive part 110f for moving the arm 110e in the up and down direction. A chuck part 110g for sandwiching and gripping the cuvette 8 is arranged at the distal end of the arm 110e.

The secondary reaction member 80b (FIGS. 1 and 2) has a configuration similar to the primary reaction member 80b, and is arranged to rotatably transport the cuvette 8 held at the holder 83a of the rotatable table 83 by a predetermined angle for every predetermined period (18 seconds in the present embodiment), and to stir the specimen, the R1 reagent, the R2 reagent, the R3 reagent, and the R5 reagent in the cuvette 8. That is, the secondary reaction member 80b is arranged to react the R3 reagent including labeled antibody and the antigen in the specimen in the cuvette 8, and to react the R5 reagent having luminescent substrate and the labeled antibody of the R3 reagent. The secondary reaction member 80b is configured by the rotatable table 83 for conveying the cuvette 8 accommodating the specimen, the R1 reagent, the R2 reagent, the R3 reagent and the R5 reagent in the rotating direction, and a container conveyance section 84 for stirring the specimen, the R1 reagent, the R2 reagent, the R3 reagent and the R5 reagent in the cuvette 8 and conveying the cuvette 8 accommodating the stirred specimen etc. to the BF separator 100b to be hereinafter described. Furthermore, the container conveyance section 84 has a function of again conveying the cuvette 8 processed by the BF separator 100b to the holder 83a of the rotatable table 83. Detailed configurations of the secondary reaction member 80b are the same as the primary reaction member 80a, and thus the description thereof will be omitted.

The reagent dispensing arm 90c (see FIGS. 1 and 2) has a function of suctioning the R3 reagent in the reagent container 7 installed at the installing section 61 of the reagent installing member 60a and dispensing the suctioned R3 reagent into the cuvette 8 dispensed with the specimen, the R1 reagent, and the R2 reagent of the secondary reaction member 80b. The reagent dispensing arm 90c includes a motor 93a, a drive transmitting part 93b connected to the motor 93a, and an arm 93d attached to the drive transmitting part 93b by way of a shaft 93c. The drive transmitting part 93b is configured to turn the arm 93d with the shaft 93c as the center by the driving force from the motor 93a, and move the arm in the up and down direction. A nozzle 93e for suctioning and discharging the R3 reagent in the reagent container 7 is attached to the distal end of the arm 93d. That is, the nozzle 93e is configured to suction the R3 reagent in the reagent container 7 through the groove 62a of the upper surface 62 of the reagent installing member 60a, and thereafter, dispense the suctioned R3 reagent into the cuvette 8 dispensed with the specimen, the R1 reagent, and the R2 reagent.

The BF separator 100b (see FIGS. 1 and 2) has a configuration similar to the BF separator 100a, and is arranged to separate the non-reactive R3 reagent (unnecessary component) and the magnetic particles from the sample in the cuvette 8 (see FIG. 7) conveyed by the container conveyance section 84 of the secondary reaction member 80b. A detailed configuration of the BF separator 100b is the same as the BF separator 100a, and thus the description thereof will be omitted.

The reagent dispensing arm 90d (see FIGS. 1 and 2) has a function of dispensing the R5 reagent containing luminescent substrate in the reagent container (not shown) installed at the lower part of the immune analyzer 1 into the cuvette 8 accommodating the specimen, the R1 reagent, the R2 reagent, and the R3 reagent of the secondary reaction member 80b. The reagent dispensing arm 90d includes a motor 94a, a drive transmitting part 94b connected to the motor 94a, and an arm 94c attached to the drive transmitting part 93b by way of a shaft. The drive transmitting part 94b is configured to turn the arm 94c with the shaft as the center by the driving force from the motor 94a, and move the arm in the up and down direction. A tube 94d for discharging the R5 reagent from the reagent container (not shown) installed at the lower part of the immune analyzer 1 into the cuvette 8 held at the holder 83a of the rotatable table 83 is attached to the distal end of the arm 94c.

The detector 120 (see FIGS. 1 and 2) is arranged to measure the amount of antigen contained in a specimen by acquiring the light generated in the reaction process of the labeled antibody bound to the antigen of the specimen performed with a predetermined process and the luminescent substrate with a photo multiplier tube. The detector 120 is configured by an installing section 121 for installing the cuvette 8 accommodating the specimen, the R1 reagent, the R2 reagent, the R3 reagent, and the R5 reagent, and a conveyance mechanism section 122 for conveying the cuvette 8 (see FIG. 6) held at the holder 83a of the rotatable table 83 of the secondary reaction member 80b. A lid 123 is arranged in an openable/closable manner at the installing section 121 so that external light does not enter the cuvette 8 installed at the installing section 121.

The waste member 130 (see FIGS. 1 and 2) is arranged to discard the cuvette 8 (see FIG. 6) accommodating the measured sample measured by the detector 120. The waste member 130 is configured by a suction part 131 (see FIG. 2) for suctioning the measured sample in the cuvette 8 and a discarding hole 132 arranged at a position of a predetermined spacing from the suction part 131. After the measured sample is suctioned by the suction part 131, the used cuvette 8 is discarded to a dust box (not shown) arranged at the lower part of the immune analyzer 1 through the discarding hole 132.

[Measurement Process]
(Cuvette Supplying Step)

First, as shown in FIGS. 1 and 2, the cuvette 8 (see FIG. 6) is guided from the hopper 71a through the inductive plate 72 to the concave part 73b of the supporting board 73 by driving the motor 71b of the hopper feeder 71 of the cuvette supply member 70. The cuvette 8 accommodated in the concave part 73b of the supporting board 73 is conveyed to the holder 81a of the rotatable table 81 of the primary reaction member 80a by the supply catcher section 74.

(R1 Reagent Dispensing Step)

Figure 8:
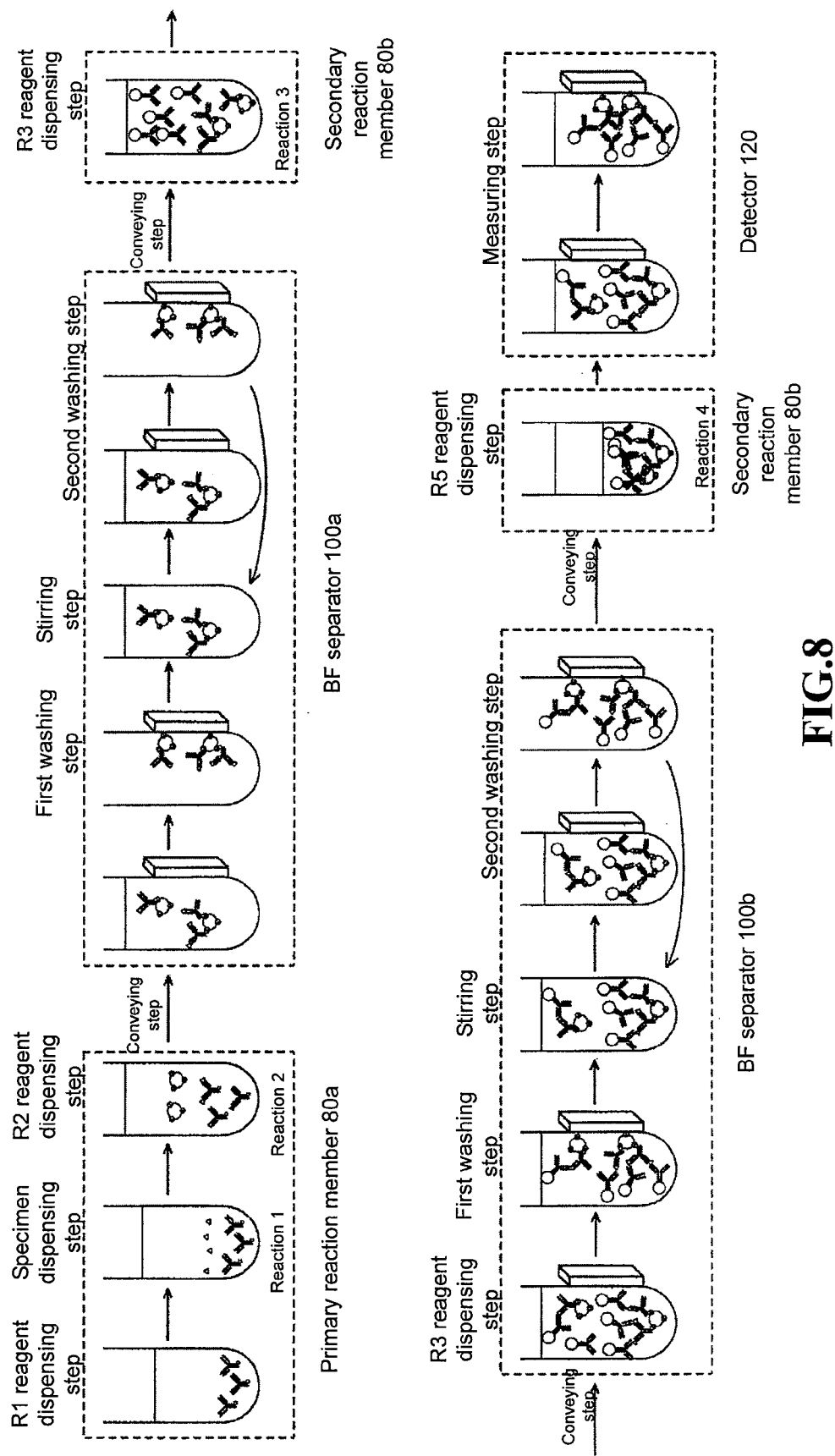
FIG. 8 is a view showing a measurement flow of the immune analyzer shown in FIG. 1.
Figure 9:
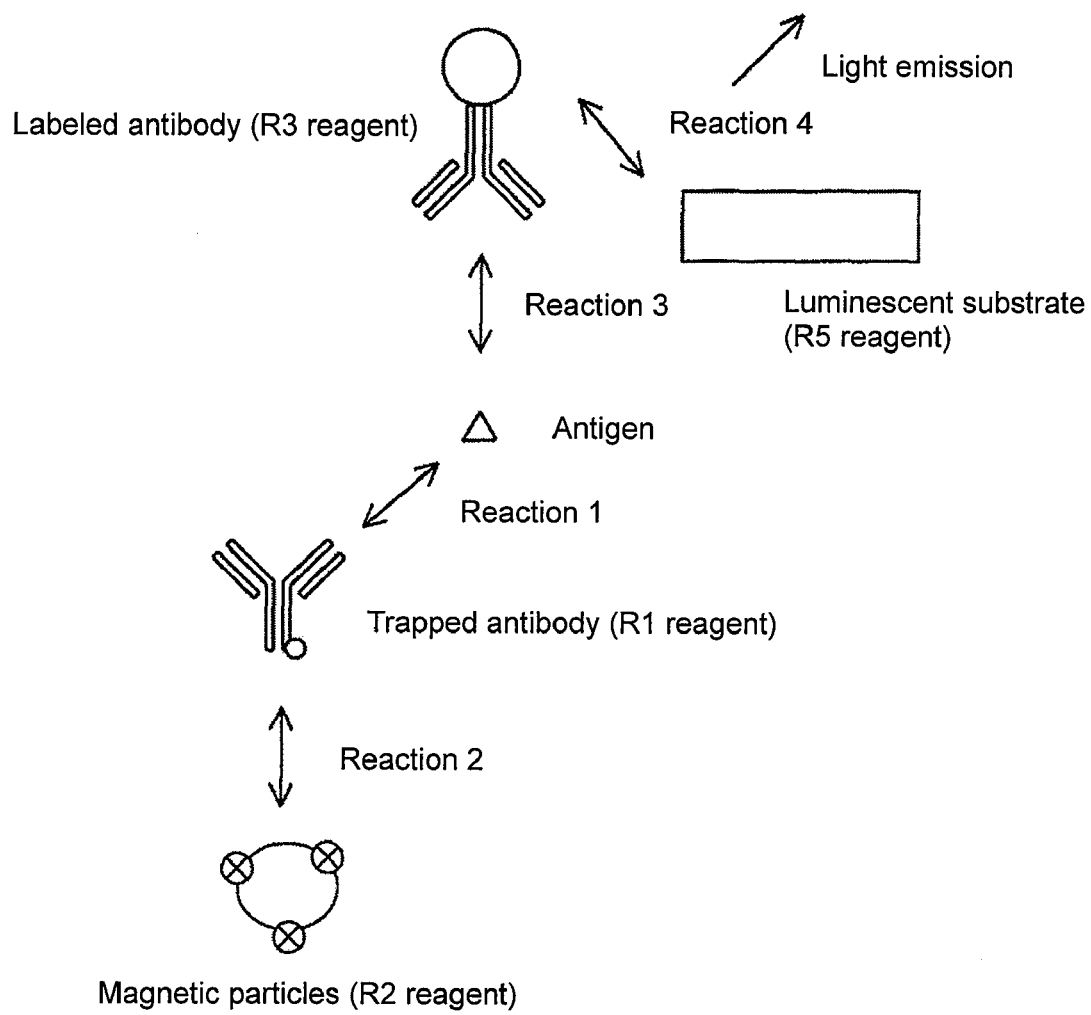
FIG. 9 is a frame format view showing a reaction between an antigen of a specimen and various reagents measured in the immune analyzer shown in FIG. 1.

After suctioning the R1 reagent in the reagent container 5 installed in the installing section 61 of the reagent installing member 60a, the reagent dispensing arm 90a is turned towards the primary reaction member 80a side to discharge the suctioned R1 reagent into the cuvette 8 conveyed by the supply catcher section 74. As shown in FIGS. 8 and 9, the R1 reagent contains trapped antibody that binds to the antigen contained in the specimen.

(Specimen Dispensing Step)

After being attached with the pipette chip 2 (see FIG. 3) conveyed to the conveyance rack of the urgent specimen/chip conveyance member 20, the specimen dispensing arm 50 suctions the specimen such as blood from the test tube 3 mounted on the rack 4 conveyed to the suction position 1a (see FIGS. 1 and 2) by the specimen conveyance member 10. The specimen dispensing arm 50 is then turned towards the primary reaction member 80a side to discharge the suctioned specimen into the cuvette 8 accommodating the R1 reagent of the holder 81a of the rotatable table 81.

(R1 Reagent and Specimen Stirring Step)

The container conveyance section 82 of the primary reaction member 80a then stirs the cuvette 8 accommodating the R1 reagent and the specimen.

(Incubation Step (Reaction 1 Shown in FIGS. 8 and 9))

The stirred R1 reagent and the specimen are then incubated for a predetermined time in the cuvette 8 of the holder 81a of the rotatable table 81 which rotates by a predetermined angle every 18 seconds. If about 162 seconds (18 seconds×9) is required for the reaction between the R1 reagent and the specimen, the cuvette 8 accommodating the R1 reagent and the specimen is rotatably transported by 9 pitches after being dispensed with specimen. Thus, the trapped antibody (R1 reagent) and the antigen of the specimen bind while the cuvette 8 is being rotatably transported.

(R2 Reagent Dispensing Step)

After suctioning the R2 reagent in the reagent container 6 installed in the installing section 64 of the reagent installing member 60b, the reagent dispensing arm 90b is turned towards the primary reaction member 80a side to discharge the suctioned R2 reagent into the cuvette 8 accommodating the R1 reagent and the specimen incubated for a predetermined time. As shown in FIGS. 8 and 9, the R2 reagent contains magnetic particles that bind to the trapped antibody bound with the antigen in the specimen.

(R2 Reagent and Specimen Stirring Step)

The container conveyance section 82 of the primary reaction member 80a then stirs the cuvette 8 accommodating the R1 reagent, the specimen, and the R2 reagent similar to the stirring step of the R1 reagent and the specimen.

(Incubation Step (Reaction 2 Shown in FIGS. 8 and 9))

The stirred R1 reagent, the specimen, and the R2 reagent are then incubated for a predetermined time in the cuvette 8 of the holder 81a of the rotatable table 81. If about 90 seconds (18 seconds×5) is required for the reaction between the trapped antibody (R1 reagent) bound with the antigen of the specimen and the magnetic particles (R2 reagent), the cuvette 8 accommodating the R1 reagent, the specimen, and the R2 reagent is rotatably transported by 5 pitches after being dispensed with the R2 reagent. Thus, the magnetic particles (R2 reagent) and the trapped antibody (R1 reagent) bound with the antigen of the specimen bind while the cuvette 8 is being rotatably transported.

(Conveying Step from Primary Reaction Member 80a to BF Separator 100a)

The cuvette 8 accommodating the incubated R1 reagent, the specimen, and the R2 reagent is conveyed to a cuvette installation hole 101d of the BF separator 100a shown in FIG. 9 by the container conveyance section 82 of the primary reaction member 80a.

(First Washing Step in BF Separator 100a)

In the present embodiment, the cuvette 8 installed in the cuvette installation hole 101d of the installing part 101a of the magnet collecting section 101 is transported in the rotating direction with the rotation of the installing part 101a, and arranged at a position corresponding to a primary stirring part 102d of the stirring mechanism section 102. In this case, the magnetic particles in the cuvette 8 held at the cuvette installation hole 101d of the installing part 101a are collected by a magnet 101b arranged on the side of the cuvette 8. After inserting a nozzle 103f of the primary washing part 103e of the primary separator 103a into the cuvette 8, the sample in the cuvette 8 is suctioned to remove unnecessary components other than the magnetic particles and the antigen binding with the magnetic particles through the trapped antibody. However, in the first washing step, some of the unnecessary components sometimes retain at the inner wall of the cuvette 8 with the magnetic particles as if being caught in the magnetic particles attracted to the magnet 101b of the magnet collecting section 101, and thus it becomes difficult to sufficiently remove the unnecessary components; therefore, a stirring step and a second washing step described below are carried out to sufficiently remove the unnecessary components in the present embodiment.

(Stirring Step in BF Separator 100a (First Time))

In the present embodiment, washing liquid is supplied into the cuvette 8 performed with the first washing step in the BF separator 100a, and stirring is performed. The unnecessary components caught in the magnetic particles and retained at the inner wall of the cuvette 8 with the magnetic particles then can be dispersed.

(Second Washing Step in BF Separator 100a (First Time))

In the present embodiment, the cuvette 8 stirred in the BF separator 100a is again held at the cuvette installation hole 101d of the magnet collecting section 101 to collect the magnetic particles on the magnet 101b side arranged on the side of the cuvette 8. After collecting the magnetic particles in the cuvette 8, washing liquid and unnecessary components are discharged.

(Stirring Step in BF Separator 100a (Second Time))

Furthermore, in the present embodiment, washing liquid is again supplied into the cuvette 8 performed with the first second washing step in the BF separator 100a, and stirring is performed.

(Second Washing Step in BF Separator 100a (Second Time))

In the present embodiment, the cuvette 8 stirred in the BF separator 100a is again held at the cuvette installation hole 101d of the magnet collecting section 101 to collect the magnetic particles on the magnet 101b side arranged on the side of the cuvette 8. After collecting the magnetic particles in the cuvette 8, washing liquid and slightly remaining unnecessary components are reliably discharged.

Subsequently, similar stirring step and the second washing step are further carried out two times each. Thereafter, the cuvette 8 accommodating the sample, which mainly contains solid-phase magnetic particles removed with unnecessary component, is transported in the rotating direction with the rotation of the installing part 101a of the BF separator 100a and conveyed to the position to be gripped by the chuck part 110g of the conveyance catcher member 110, as shown in FIGS. 1 and 2.

(Conveying Step from BF Separator 100a to Secondary Reaction Member 80b)

The cuvette 8 in which separation of the unnecessary components and the magnetic particles is performed by the BF separator 100a is gripped by the chuck part 110g of the conveyance catcher member 110 and conveyed to the holder 83a of the rotatable table 83 of the secondary reaction member 80b, as shown in FIGS. 1 and 2.

(R3 Reagent Dispensing Step)

After suctioning the R3 reagent in the reagent container 7 installed in the installing section 61 of the reagent installing member 60a, the reagent dispensing arm 90c is turned towards the secondary reaction member 80b side to discharge the suctioned R3 reagent into the cuvette 8 accommodating the magnetic particles (R2 reagent) bound through the trapped antibody (R1 reagent) and the antigen of the specimen. As shown in FIGS. 8 and 9, the R3 reagent contains labeled antibody that binds to the antigen in the specimen.

(R3 Reagent and Specimen Stirring Step)

The container conveyance section 84 of the secondary reaction member 80b then stirs the cuvette 8 accommodating the trapped antibody (R1 reagent), the antigen (specimen), the magnetic particles (R2 reagent), and the R3 reagent containing the labeled antibody, similar to the stirring step of the R1 reagent and the specimen described above.

(Incubation Step (Reaction 3 Shown in FIGS. 8 and 9))

The stirred trapped antibody (R1 reagent), the antigen (specimen), the magnetic particles (R2 reagent), and the R3 reagent containing the labeled antibody are then incubated for a predetermined time in the cuvette 8 of the holder 83a of the rotatable table 83, as shown in FIGS. 1 and 2. If about 198 seconds (18 seconds×11) is required for the reaction between the antigen of the specimen and the labeled antibody (R3 reagent), the cuvette 8 accommodating the trapped antibody (R1 reagent), the antigen (specimen), the magnetic particles (R2 reagent), and the R3 reagent containing the labeled antibody is rotatably transported by 11 pitches after being dispensed with the R3 reagent. Thus, the antigen bound with the magnetic particles (R2 reagent) through the trapped antibody (R1 reagent) and the labeled antibody (R3 reagent) bind while the cuvette 8 is being rotatably transported.

(Conveying Step from Secondary Reaction Member 80B to BF Separator 100b)

The cuvette 8 accommodating the incubated trapped antibody (R1 reagent), the antigen (specimen), the magnetic particles (R2 reagent), and the R3 reagent containing the labeled antibody is conveyed to the cuvette installation hole 101d of the BF separator 100b by the container conveyance section 84 of the secondary reaction member 80b, similar to the conveying step from the primary reaction member 80a to the BF separator 100a described above.

(First Washing Step, Stirring Step, and Second Washing Step in BF Separator 100b)

In the present embodiment, similar to the first washing step, the four stirring steps, and the second washing step in the BF separator 100a, the first washing step, four stirring steps, and the second washing step are performed in the BF separator 100b. Thus, the R3 reagent (unnecessary component) containing the labeled antibody that does not bind with the antigen of the specimen can be sufficiently removed. Thereafter, the cuvette 8 accommodating the sample containing the antigen bound with the labeled antibody removed with unnecessary components is transported in the rotating direction with the rotation of the magnet collecting section of the BF separator 100*b*, and conveyed to a position to which it can be conveyed by the container conveyance section 84 of the secondary reaction member 80*b*.

(Conveying Step from BF Separator 100*a* to Secondary Reaction Member 80*b*)

The cuvette 8 in which separation of the unnecessary components and the magnetic particles is performed by the BF separator 100*b* is again conveyed to the holder 83*a* of the rotatable table 83 by the container conveyance section 84 of the secondary reaction member 80*b* as shown in FIGS. 1 and 2.

(R4 Reagent Dispensing Step)

The reagent dispensing arm discharges the R4 reagent (dispersion liquid) in the reagent container (not shown) installed at the lower part of the immune analyzer 1 to the cuvette 8 accommodating the trapped antibody (R1 reagent), the magnetic particles (R2 reagent), the labeled antibody (R3 reagent), and the antigen of specimen.

(R4 Reagent and Labeled Antibody Stirring Step)

The container conveyance section 84 of the secondary reaction member 80*b* then stirs the cuvette 8 accommodating the trapped antibody (R1 reagent), the antigen (specimen), the magnetic particles (R2 reagent), the labeled antibody (R3 reagent), and the R4 reagent, similar to the stirring step of the R1 reagent and the specimen described above.

(R5 Reagent Dispensing Step)

The reagent dispensing arm 90*d* discharges the R5 reagent containing luminescent substrate in the reagent container (not shown) installed at the lower part of the immune analyzer 1 to the cuvette 8 accommodating the trapped antibody (R1 reagent), the magnetic particles (R2 reagent), the labeled antibody (R3 reagent), the dispersion liquid (R4 reagent), and the antigen of specimen through a tube 94*d*. As shown in FIGS. 8 and 9, the R5 reagent contains the luminescent substrate that emits light by reacting with the labeled antibody of the R3 reagent.

(Stirring Step of R5 Reagent and Labeled Antibody)

The container conveyance section 84 of the secondary reaction member 80*b* stirs the cuvette 8 accommodating the trapped antibody (R1 reagent), the antigen (specimen), the magnetic particles (R2 reagent), the labeled antibody (R3 reagent), the dispersion liquid (R4 reagent), and the R5 reagent containing the luminescent substrate, similar to the stirring step of the R1 reagent and specimen described above.

(Incubation Step (Reaction 4 Shown in FIGS. 14 and 15))

The stirred trapped antibody (R1 reagent), the antigen (specimen), the magnetic particles (R2 reagent), the dispersion liquid (R4 reagent), the labeled antibody, and the R5 reagent containing the luminescent substrate are then incubated for a predetermined time in the cuvette 8 of the holder 83*a* of the rotatable table 83. If about 378 seconds (18 seconds×21) is required for the reaction between the labeled antibody (R3 reagent) bound to the antigen of the specimen and the luminescent substrate (R5 reagent), the cuvette 8 accommodating the trapped antibody (R1 reagent), the antigen (specimen), the magnetic particles (R2 reagent), the labeled antibody (R3 reagent), and the R5 reagent containing the luminescent substrate is rotatably transported by 21 pitches after being dispensed with the R5 reagent. Thus, the reaction between the labeled antibody (R3 reagent) and the luminescent substrate (R5 reagent) advances while the cuvette 8 is being rotatably transported.

(Measuring Step)

Subsequently, as shown in FIGS. 1 and 2, the cuvette 8 accommodating the incubated trapped antibody (R1 reagent), the antigen (specimen), the magnetic particles (R2 reagent), the labeled antibody (R3 reagent), the dispersion liquid (R4 reagent), and the R5 reagent containing the luminescent substrate is conveyed to the installing section 121 by the conveyance mechanism section 122 of the detector 120. In measurement, the lid 123 is closed to obtain a state in which the interior of the installing section 121 is shielded from the external light, whereby measurement can be performed under the condition the external light is shielded. In this case, the magnetic particles in the cuvette 8 installed at the installing section 121 is attracted towards the magnet side. Thus, when measuring the light emission amount generated in the reaction process of the labeled antibody of the R3 reagent and the luminescent substrate of the R5 reagent, the measurement of the light emission amount is suppressed from being inhibited by the magnetic particles. Under such a condition, the light emission amount (amount proportional to the number of photons) generated in the reaction process of the labeled antibody of the R3 reagent and the luminescent substrate of the R5 reagent is acquired with the photo multiplier tube (not shown).

(Discarding Step)

As shown in FIGS. 1 and 2, the cuvette 8 accommodating the measured sample performed with measurement is conveyed to the position below the suction part 131 (see FIG. 2) of the waste member 130 by the conveyance mechanism section 122 of the detector 120. The suction part 131 of the waste member 130 moves downward, suctions the measured sample, and empties the cuvette 8. Thereafter, the conveyance mechanism section 122 of the detector 120 gripping the empty cuvette 8 is turned to be conveyed up to the position corresponding to the discarding hole 132 of the waste member 130, and thereafter, caused to drop the empty cuvette 8 into the discarding hole 132 to discard the used cuvette 8 into the dust box (not shown) arranged at the lower part of the immune analyzer 1 through the discarding hole 132.

The features of the present embodiment lie in providing an ID number (calibration curve specifying information) specifying the calibration curve to the calibration curve created by the CPU 401*a* of the control section 400*a*, and storing the analysis result and the calibration curve specifying information provided to the calibration curve used in the analysis in correspondence to each other.

The calibration curve used in the analysis is specified by the calibration curve specifying information in such manner, and the calibration curve specifying information and the analysis result are stored in correspondence to each other, so that it becomes easy to recognize which calibration curve was used to analyze a certain analysis result, whereby the traceability of the analysis result improves. As a result, if found that abnormality of the analysis result resulted from the inappropriate calibration curve, the analysis result using the relevant calibration curve is specified and re-analysis can be easily performed.

[Registration of Calibration Curve]

Figure 10:
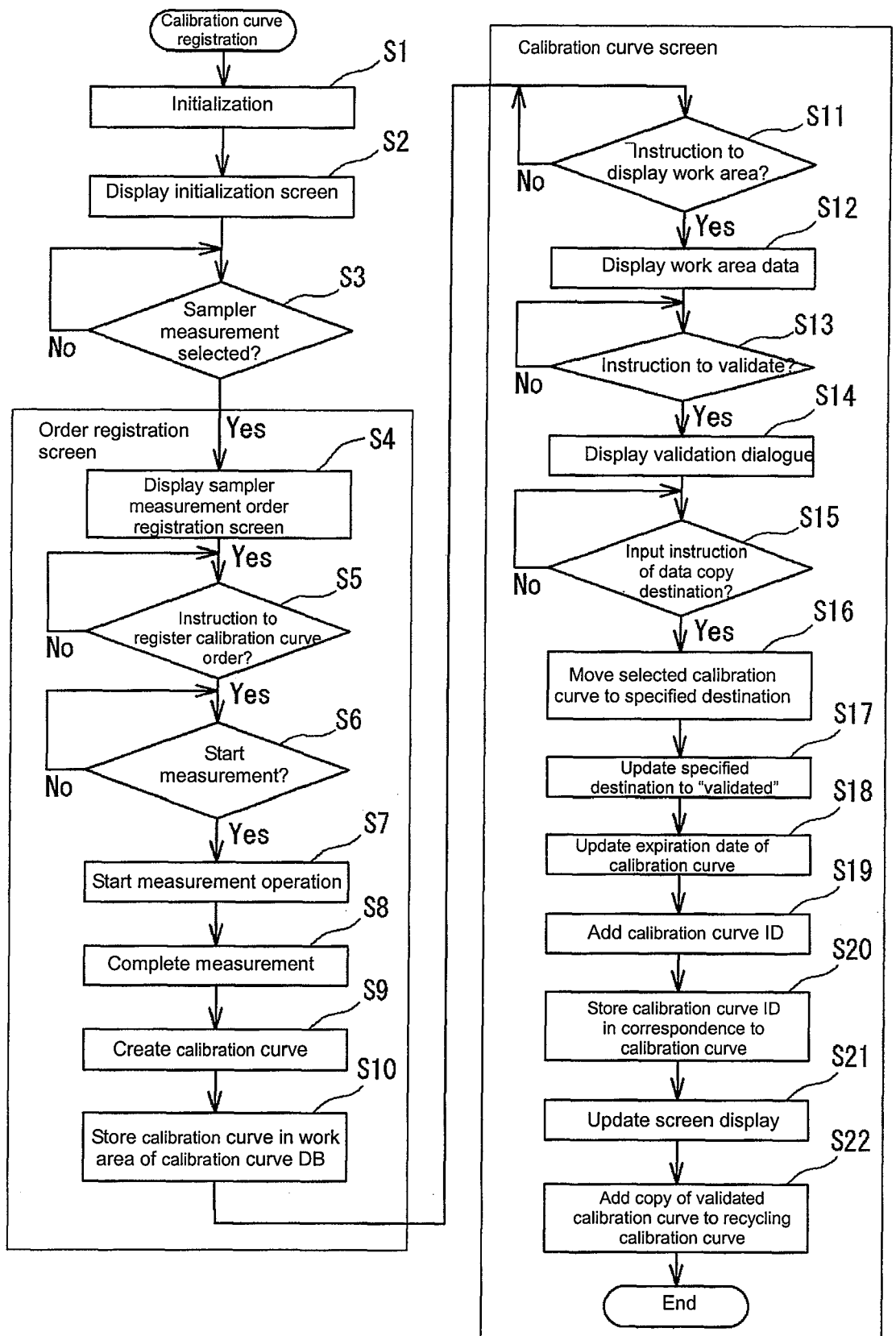
FIG. 10 is a view showing a flow of creating the calibration curve and providing calibration curve specifying information to the calibration curve in the present embodiment.

The provision of the calibration curve specifying information is carried out in the following manner. FIG. 10 is a view showing a flow of creating the calibration curve, providing the calibration curve specifying information to the calibration curve, and registering the calibration curve in the present embodiment.

Figure 11:
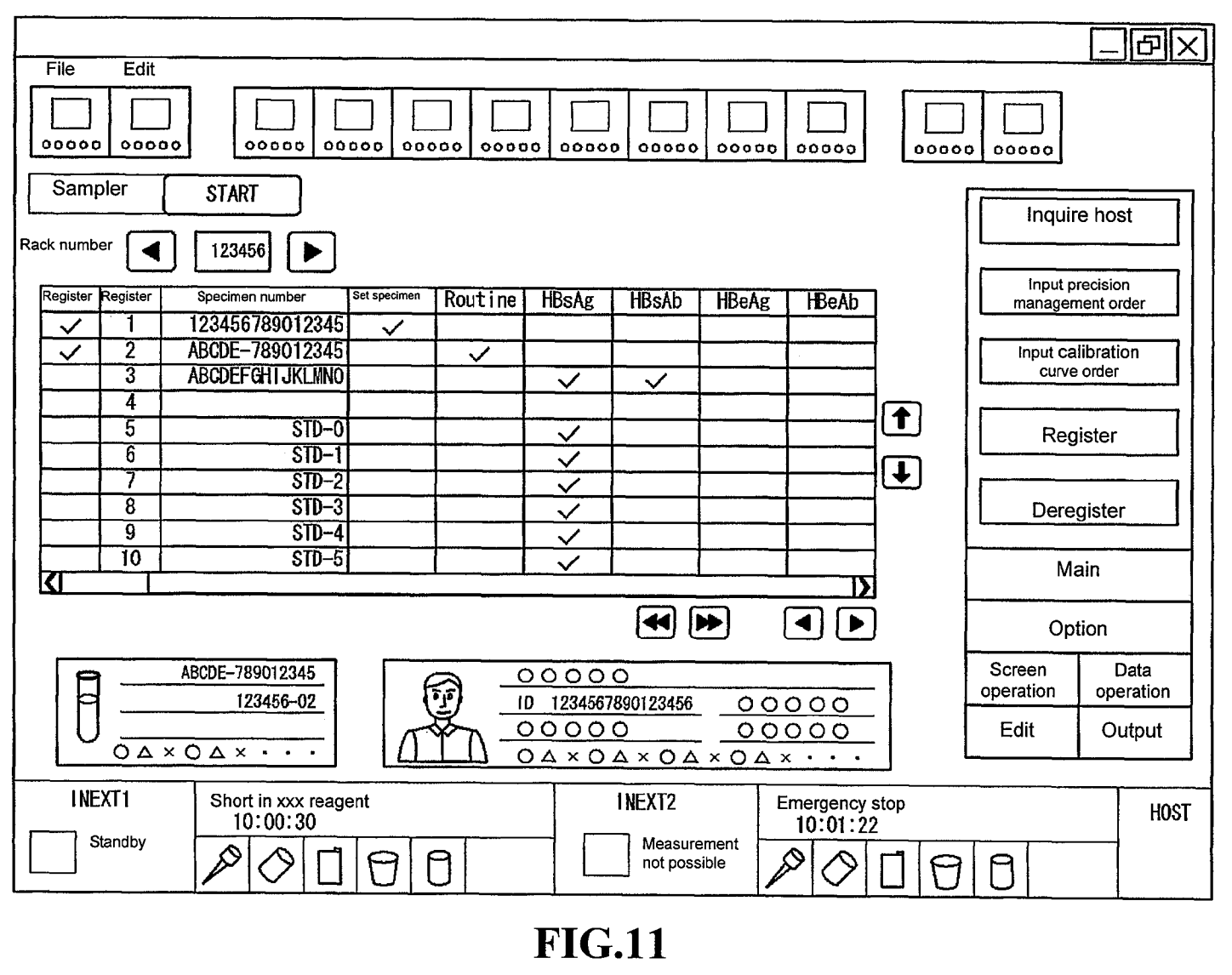

First, when the user turns on the power (not shown) of the control device 4, initialization (initialization of program) of the control section 4*a* is executed (step S1), and an initialization screen (not shown) is displayed (step S2). When sampler measurement is selected by the user on the initialization screen (Yes in step S3), the control section 400a displays an order registration screen for sampler measurement shown in FIG. 11 (step S4).

When the user clicks "input calibration curve order" on the order registration screen, a calibration curve order input dialogue shown in FIG. 12 is displayed on the display member 400b. After designation of measurement order for creating the calibration curve such as measurement item name, lot number of reagent, and calibration curve creating method is input by the user (Yes in step S5), and instruction to start measurement is input (Yes in step S6) in this calibration curve order input dialogue, the measurement unit starts the measurement operation according to the specified order (step S7).

Figure 13:
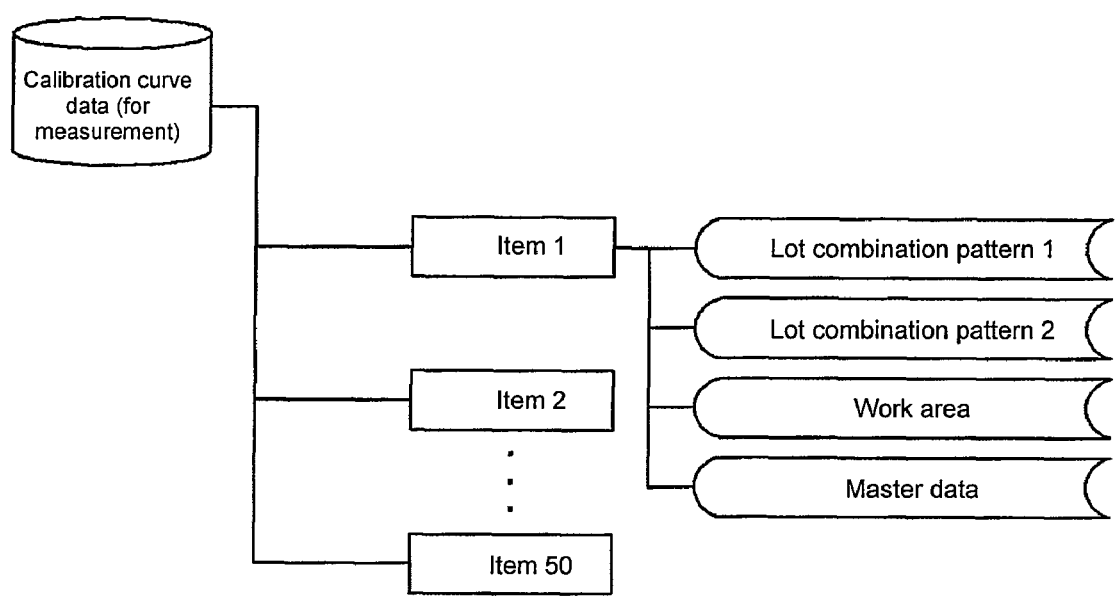
FIG. 13 is a view showing a configuration of a measurement calibration curve database.

Subsequently, after the measurement is completed in step S8, the control section 400a creates the calibration curve using the measurement data (step S9), and stores the calibration curve in the work area (see FIG. 13) of the calibration curve database (step S10). The calibration curve database has a configuration shown in FIG. 13, where four types of files are stored for every fifty measurement items. The application of each file is "lot combination pattern 1 (lot 1)", "lot combination pattern 2 (lot 2)", "work area" and "master data". Among them, "lot combination pattern 1 (lot 1)" and "lot combination pattern 2 (lot 2)" maintain a calibration curve that can be used to calculate concentration. Regarding five types of reagents R1 to R5, R1 to R3 reagents constitute a set, and R4 and R5 reagents constitute a set. In changing reagents, the reagents are changed in units of sets. When changing either reagent sets of R1 to R3 reagents or R4 and R5 reagents, there is a period in which the old and new reagent sets are not yet completely changed, and the reagent set (old set) scheduled to be changed and the new reagent set coexist in the apparatus. In this case, in time of switching the lots of the reagents, two lot combination patterns exist for the reagent set in the apparatus. The files of pattern 1 and pattern 2 thus are provided to store the calibration curve corresponding to both combinations.

The "work area" is a file for temporarily holding data of newly measured calibration curve measurement, data restoring backup file, data reproduced with a recycling function to be hereinafter described, and corrected data, and cannot be used to calculate concentration.

Furthermore, "master data" holds data used as a base of one point shift which is a simple measurement method (method of specifying only one coordinate with a calibrator and obtaining the calibration curve graph from the coordinate and the slope of the calibration curve graph obtained in the past on the assumption that the slope of the calibration curve graph is equal to the slope of the calibration curve graph obtained in the past) in time of calibration curve measurement. The master data is created by master registering the calibration curve of lot 1, lot 2, or work area. Such master data cannot be used to calculate the concentration.

Figure 14:
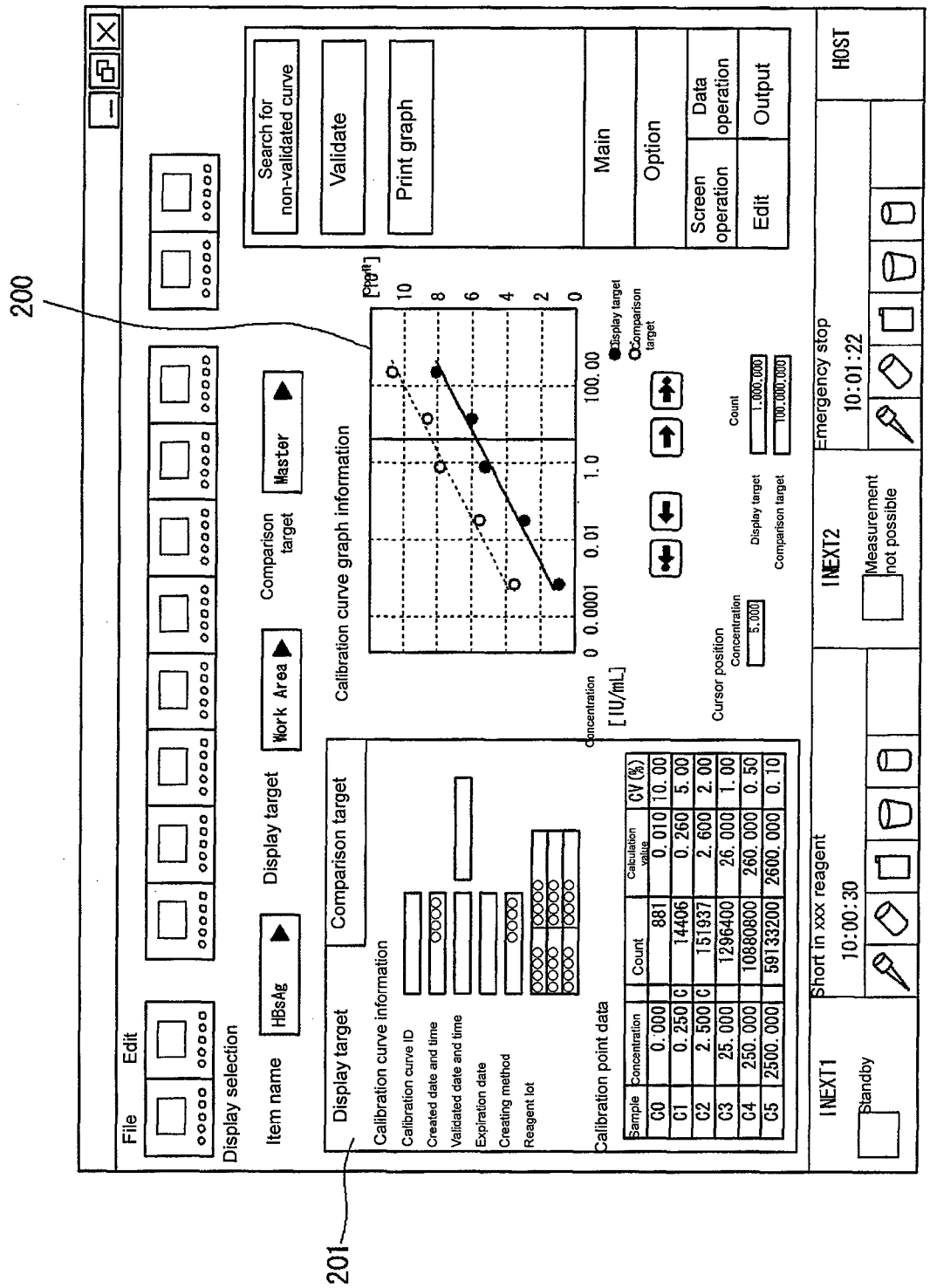
FIG. 14 is a view showing an example of a calibration curve screen.

When the user inputs instruction to display the work area (step S11), the work area data is displayed on the calibration curve screen as shown in FIG. 14 (step S12). The calibration curve screen includes a graph display region 200 for displaying the graph of the calibration curve, and a specifying information display region 201 such as calibration curve ID, which is calibration curve specifying information provided to the relevant calibration curve, and reagent lot. At this point, the calibration curve ID is not provided and the calibration curve ID is not displayed in the specifying information display region 201 of the work area. The user can easily check whether or not the calibration curve is appropriate by referencing the graph, and can also check the calibration curve specifying information of the relevant calibration curve by displaying the graph of the calibration curve and the calibration curve specifying information provided to the relevant calibration curve.

Subsequently, in the calibration curve screen, when the user instructs validation of the calibration curve data of the work area by clicking "validate" (Yes in step S13), a validation dialogue of the calibration curve shown in FIG. 15 is displayed on the display member 400b (step S14).

In the validation dialogue, when the user specifies the copy destination of the calibration curve (Yes in step S15), the control section 400a moves the calibration curve data to the specified lot of lot 1 or lot 2 (step S16). The control section then updates the lot of the specified destination to "validated" (step S17). Specifically, "validated date and time" is written in the screen ("display target" on the upper part is changed from work area to lot 1 or lot 2) corresponding to the calibration curve screen shown in FIG. 14, and "validated" is written in place of "not validated" on the right side thereof. The control section 400a then sets an expiration date of the calibration curve of a predetermined period (e.g., 30 days) from the relevant date, and updates the expiration date of the calibration curve in the calibration curve screen (step S18).

After the calibration curve is confirmed, that is, validated, the control section 400a provides the calibration curve ID or the calibration curve specifying information to the calibration curve (step S19), stores the calibration curve ID in the corresponding area (lot 1 or lot 2) of the calibration curve database in correspondence with the calibration curve (step S20), and updates the display to the calibration curve screen displaying the stored calibration curve ID (step S21). Thereafter, a copy of the validated calibration curve is added to the recycling calibration curve database to be hereinafter described (step S22), and the process of providing the calibration curve ID is terminated.

[Analyzing Step]

In the present embodiment, the measurement data (number of counts of photons) obtained in the measuring step described above is analyzed based on the calibration curve to obtain the concentration (analysis result) of the antigen contained in the specimen. Specifically, the measurement data in the measurement unit is transmitted from the measurement unit to the data processing unit (control device). The control device is stored with calibration curve created in advance (created by the CPU 401a of the control section 400a based on the measurement data of when the measurement standard sample which is a mixture of standard sample (calibrator) and reagent is measured by the measurement unit). The control section 400a of the control device reads the calibration curve that matches the sample lot of the transmitted measurement data, converts the concentration of the antigen to be measured from the measurement data and the read calibration curve, and stores the result (analysis result).

Figure 16:
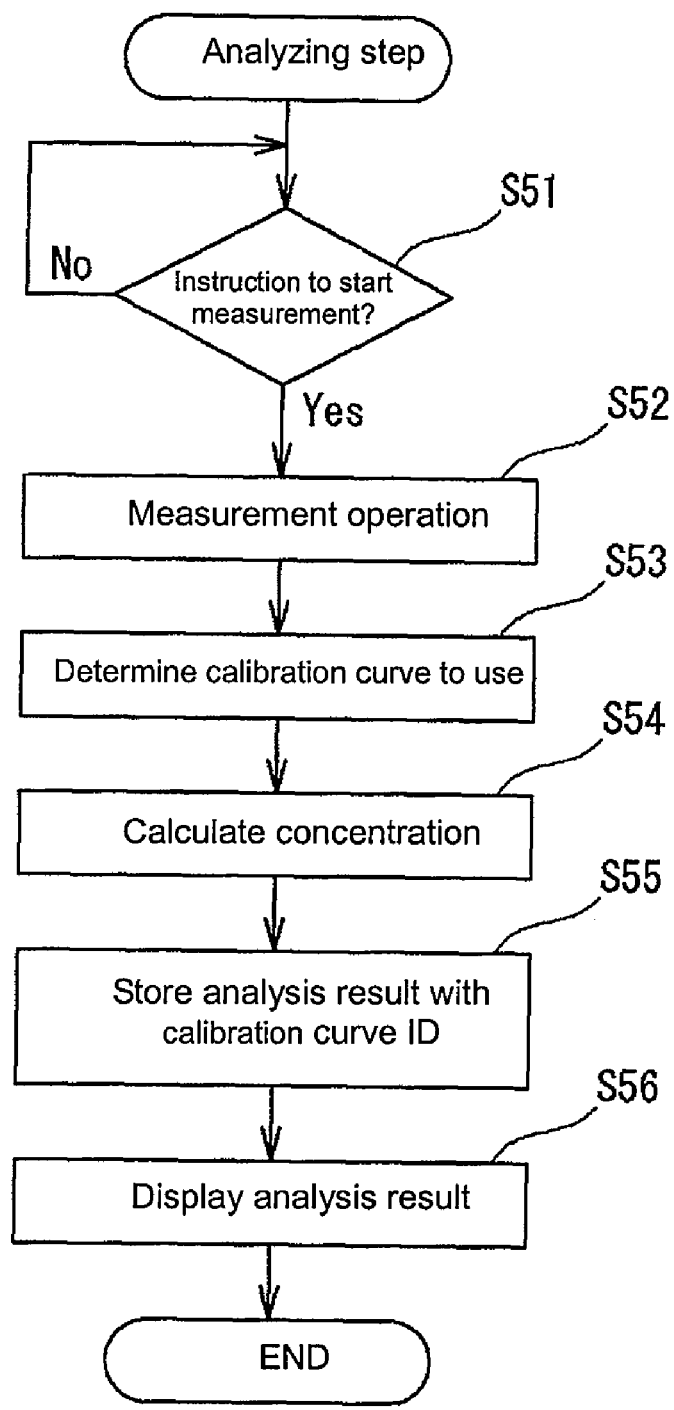
FIG. 16 is a view showing a flow of an analyzing step.

FIG. 16 is a view showing a flow of the analyzing step in the present embodiment. First, the user operates the keyboard 400c and inputs the instruction to start measurement (Yes in step S51). When accepting the instruction to start measurement, the control section 400a transmits a command to start measurement to the measurement unit, and the measurement operation described above is executed by the measurement unit (step S52). The measurement data obtained by measuring the specimen with the measurement unit is transmitted to the control device 400. The control section 400a receives the measurement data, and determines the calibration curve to use of the calibration curves stored in lot 1 and lot 2 of the calibration curve database from the lot number of the reagent used in the relevant measurement (step S53). The control section 400a then obtains the concentration from the photon count value of the measurement data using the calibration curve (step S54). The analysis result obtained in this manner is stored in the analysis result database in correspondence to the calibration curve ID of the used calibration curve (step S55), the analysis result is displayed on the screen (step S56), and the process is terminated. The calibration curve used in step S53 may be a calibration curve reproduced through recycling of the calibration curve as hereinafter described.

[Recycling of Calibration Curve]

Figure 17:
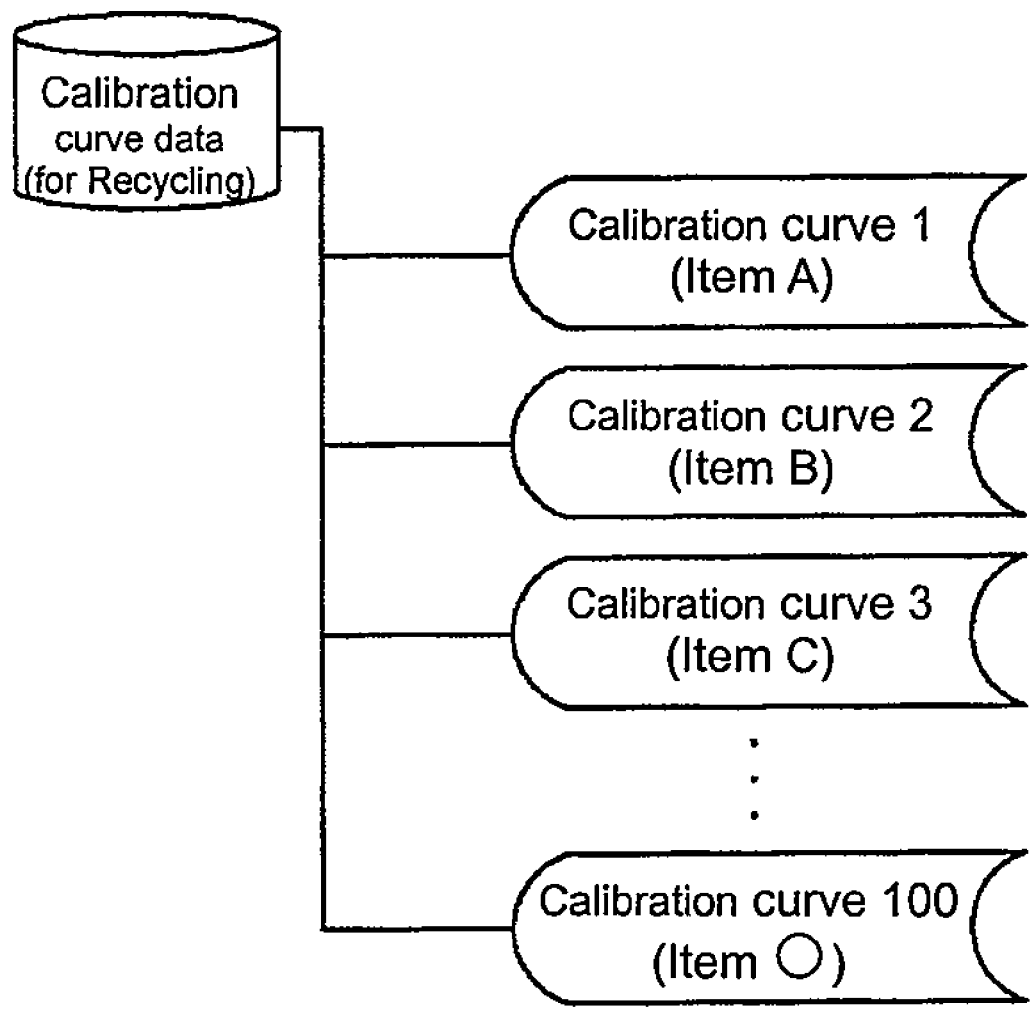
FIG. 17 is a view showing a configuration of a recycling calibration curve database.

In the present embodiment, the confirmed calibration curve is stored in the calibration curve database for storing a predetermined number of calibration curves used in the analysis, and a copy of the confirmed calibration curve is stored in a recycling calibration curve database. The recycling calibration curve database is stored with calibration curve data currently being used as well as the calibration curve data used in the past as shown in FIG. 17.

In the present embodiment, the calibration curves used in the past are stored in the second storage means, designation of a desired calibration curve of the calibration curves stored in the second storage means is accepted by the designation accepting means, and the calibration curve specified by the calibration curve recycling means is stored in the first storage means as a calibration curve that can be used for analysis. Since the calibration curve can be reproduced by the reproducing means for reproducing (recycling) the calibration curve when the calibration curve used in the past for analyzing the measurement data match, the standard sample does not need to be newly measured and the calibration curve does not need to be created. The consumption of the standard sample and the reagent thus can be suppressed, and trouble and time necessary for measuring the standard sample can be reduced.

Figure 18:
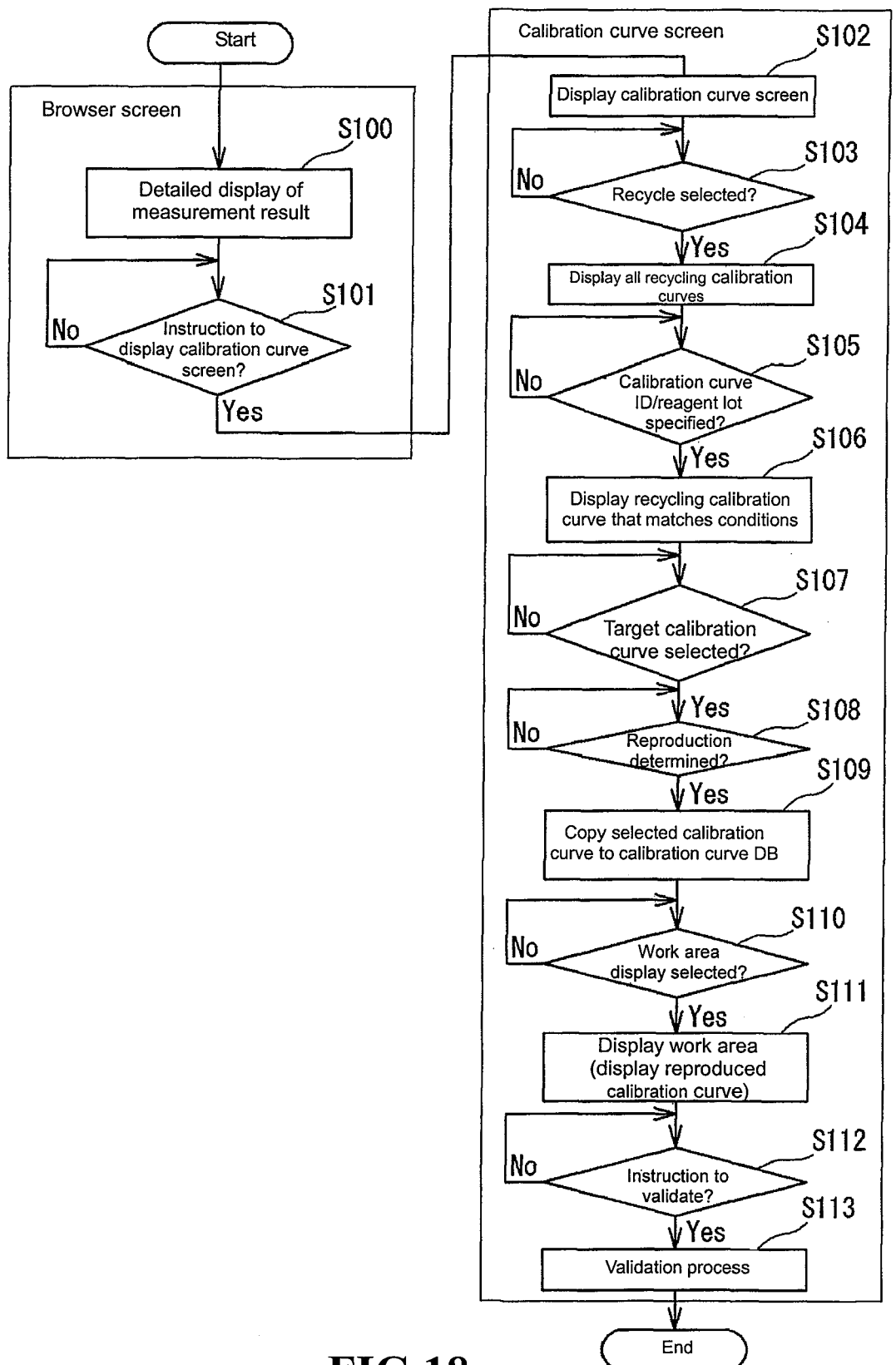
FIG. 18 is a view showing a flow of recycling the calibration curve used in the past.

The recycling of the calibration curve can be carried out in the following manner. FIG. 18 is a view showing a flow of recycling the calibration curve used in the past in the present embodiment.

First, the user displays a browser screen shown in FIG. 19 on the display 400b and checks the details of the analysis result (step S100). The browser screen (analysis result display screen) includes an analysis result list table 202 for displaying a list of analysis results. The analysis result list table 202 is displayed with the calibration curve ID of the calibration curve used in the analysis and the reagent lot along with the analysis result for every analyzing item. The user can then check the calibration curve ID and the reagent lot. The user inputs instruction to display the calibration curve screen after checking, and the control section 400a accepts the input (Yes in step S101) and displays the calibration curve screen on the display 400b (step S102). When the user selects "calibration curve recycle" from "execute" in the menu bar to select recycling of the calibration curve, such selection is accepted by the control section 400a (Yes in step S103), and a calibration curve recycle dialogue shown in FIG. 20 is displayed. All the calibration curves stored in the recycling calibration curve database described above are displayed on the calibration curve recycle dialogue (step S104).

When the calibration curve ID or the reagent lot is specified by the user, such designation is accepted by the control section 400a (Yes in step S105), and the recycling calibration curve that matches the specifying condition is displayed (step S106). The user can easily find the desired calibration curve by having the calibration curve stored in the recycling calibration curve database searchable with the calibration curve ID or the calibration curve specifying information, lot number of reagent, created date and time of calibration curve, validated date and time, calibration curve expiration date, lot number of calibrator etc. as the key. In the present embodiment, the calibration curve, calibration curve ID, lot information of reagent used in the measurement of the measurement standard sample, created date and time of calibration curve, validated date and time, calibration curve expiration date, and lot number of calibrator are stored in a correspondence manner in the recycling calibration curve database. In this case, if the lot information of the reagent used in creating the calibration curve desired to be reproduced and the created date and time of the calibration curve are known, the target calibration curve can be easily searched from the lot information and the created date and time of the calibration curve, and the like.

After the target calibration curve is selected from the displayed calibration curves by the user (Yes in step S107), and reproduction determination of the selected calibration curve is input (Yes in step S108), the control section 400a copies the selected recycling calibration curve to the calibration curve database (step S109).

When the display of the work area is selected by the user (Yes in step S110), the control section 400a causes the display 400b to display the work area (display recycled calibration curve) (step S111).

When the user makes an instruction to validate (Yes in step S112), the control section 400a moves the calibration curve of the work area to the specified destination (lot 1 or lot 2) and updates the specified destination to "validated" in step S113, similar to steps S14 to 18 in the flow of calibration curve registration. The calibration curve used in the past thereby can be recycled and used in analysis of the measurement data. For instance, if it is known that the difference (difference between lots) in nature between the current reagent and the reagent used in the past is small, the reagent for creating the calibration curve does not need to be consumed because the calibration curve used in the past can be recycled.

In the present embodiment, a configuration of storing the analysis result of the immune analyzer and the calibration curve ID used for the analysis in correspondence to each other has been described, but is not limited thereto, and a configuration of providing the calibration curve ID to the calibration curve and storing the analysis result and the calibration curve ID in correspondence to each other in the blood coagulation analyzer of adding the reagent to the sample (blood plasma) and optically measuring the process of coagulation of the sample, for example by measuring absorbance and scattering light of the sample, and converting the measurement data to the concentration of the substance to be measured using the calibration curve obtained by measuring the standard substance in advance may be adopted.

In the present embodiment, a configuration of storing the calibration curve used in the past in the recycling calibration curve database, searching for the target calibration curve with the calibration curve ID and the reagent lot number as the key from the recycling calibration curve database when reproducing the calibration curve, and copying the searched calibration curve in the calibration curve database has been described, but is not limited thereto, and a configuration of performing reproduction of the calibration curve by storing the measurement data of the calibrator used in creating the calibration curve used in the past in the recycle database, searching for the target measurement data with the calibration curve ID and the reagent lot number as the key from the recycle database when reproducing the calibration curve, creating the calibration curve using the searched measurement data, and storing the calibration curve in the calibration curve database may be adopted. In this case, the measurement data of the measurement standard sample, the calibration curve ID, the lot information of the reagent used in measuring the measurement standard sample, the created date and time of the calibration curve, the validated date and time, the calibration curve expiration date, and the lot number etc. of the calibrator may be stored in the recycle database in correspondence to each other. The measurement data of the target measurement standard sample can be easily searched from the lot information and the calibration curve created date and time if the lot information of the reagent used in creating the calibration curve to be reproduced, the created date and time of the calibration curve, and the like are known.

What is claimed is:

1. A sample analyzer comprising:
a measurement unit configured to:
obtain first measurement data, comprising measuring a measurement standard sample including a standard sample and a reagent;
obtain second measurement data, comprising measuring a measurement sample including a sample and the reagent by the measurement unit;
a computer processor in communication with the measurement unit; and
a memory in communication with the computer processor, the computer processor comprising instructions that, when executed, cause the computer processor to:
generate a calibration curve based on the first measurement data;
provide calibration curve specifying information corresponding to the calibration curve;
obtain an analysis result by processing the second measurement data based on the calibration curve; and
store, on the memory, the acquired analysis result in correspondence to the calibration curve specifying information corresponding to the calibration curve used in the process of the second measurement data.

2. The sample analyzer according to claim 1, wherein the instructions, when executed, further caused the computer processor to display a calibration curve information display screen including a graph display region for displaying a graph of the calibration curve and a specifying information display region for displaying the calibration curve specifying information provided to the calibration curve.

3. The sample analyzer according to claim 1, wherein the instructions, when executed, further caused the computer processor to:
accept validation of the calibration curve; and
when the validation of the calibration curve is accepted:
set a validation state in correspondence to the calibration curve; and
provide the calibration curve specifying information to the calibration curve.

4. The sample analyzer according to claim 1, wherein the instructions, when executed, further caused the computer processor to:
store in a first database located on the memory the calibration curve that can be used for analysis;
store in a second database located on the memory a plurality of second calibration curves used in the past;
accept designation of a specific calibration curve from the plurality of second calibration curves stored in the second database; and
store the specific calibration curve specified from the plurality of second calibration curves to the first database as the calibration curve that can be used for analysis.

5. The sample analyzer according to claim 4, wherein
the second database is configured to store the second calibration curve in correspondence to the calibration curve specifying information; and
the instructions, when executed, further caused the computer processor to search the specific calibration curve stored in the second database by the calibration curve specifying information as a key.

6. The sample analyzer according to claim 4, wherein the second database is configured to store the second calibration curve, the calibration curve specifying information, and lot information of the reagent used in the measurement of the standard sample in correspondence to one another.

7. The sample analyzer according to claim 1, the instructions, when executed, further caused the computer processor to:
store in a first database on the memory the calibration curve which can be used for analysis;
store in a second database on the memory the first measurement data of the plurality of standard samples used in creating a plurality of second calibration curves used in the past;
accept designation of a specific measurement data from the plurality of first measurement data stored in the second database;
create a third calibration curve based on the specific measurement data specified from the plurality of first measurement data stored in the second database; and
store the third calibration curve in the first database as the calibration curve which can be used for analysis.

8. The sample analyzer according to claim 7, wherein
the second database is configured to store the first measurement data of the standard sample in correspondence to the calibration curve specifying information; and
the instructions, when executed, further caused the computer processor to search the specific first measurement data stored in the second database by the calibration curve specifying information as a key.

9. The sample analyzer according to claim 7, wherein the second database is configured to store the first measurement data of the standard sample, the calibration curve specifying information, and lot information of the reagent used in the measurement of the standard sample in correspondence to one another.

10. The sample analyzer according to claim 1, wherein the instructions, when executed, further caused the computer processor to display on a display device in communication with the computer processor the analysis result and the calibration curve specifying information in correspondence to each other.

11. The sample analyzer according to claim 10, wherein the instructions, when executed, further caused the computer processor to display the lot information of the reagent used in the measurement of the standard sample in correspondence to the analysis result and the calibration curve specifying information.

12. The sample analyzer according to claim 1, wherein the instructions, when executed, further caused the computer processor to acquire the analysis result by converting the second measurement data to a concentration of a predetermined component contained in the sample based on the calibration curve.

* * * * *